United States Patent
Jones et al.

(10) Patent No.: US 12,321,791 B1
(45) Date of Patent: Jun. 3, 2025

(54) MONITORING AND AUTOMATIC UPDATING OF AN APPLICATION PROGRAMMING INTERFACE

(71) Applicant: Medcurio, Inc., Oakland, CA (US)

(72) Inventors: Kristen Michelle Jones, Coeur d'Alene, ID (US); Colin James Parker, Idyllwild, CA (US); Christa Ann Bruce, Oakland, CA (US); Walter Francis Stewart, Oakland, CA (US)

(73) Assignee: Medcurio, Inc., Oakland, CA (US)

( * ) Notice: Subject to any disclaimer, the term of this patent is extended or adjusted under 35 U.S.C. 154(b) by 122 days.

(21) Appl. No.: 17/344,783

(22) Filed: Jun. 10, 2021

Related U.S. Application Data

(63) Continuation of application No. 17/344,663, filed on Jun. 10, 2021.

(60) Provisional application No. 63/038,349, filed on Jun. 12, 2020.

(51) Int. Cl.
*G06F 16/23* (2019.01)
*G06F 9/54* (2006.01)
*G06F 16/245* (2019.01)
*G06F 16/25* (2019.01)
*G16H 10/60* (2018.01)

(52) U.S. Cl.
CPC ............ *G06F 9/54* (2013.01); *G06F 16/2365* (2019.01); *G06F 16/245* (2019.01); *G06F 16/258* (2019.01); *G16H 10/60* (2018.01)

(58) Field of Classification Search
CPC .. G06F 16/245; G06F 16/258; G06F 16/2365; G06F 9/54; G16H 10/60
See application file for complete search history.

(56) References Cited

U.S. PATENT DOCUMENTS

| | | | |
|---|---|---|---|
| 6,564,219 B1 * | 5/2003 | Lee | G06F 16/25 707/769 |
| 7,103,607 B1 * | 9/2006 | Kirkwood | G06Q 10/00 707/999.102 |
| 9,513,941 B2 * | 12/2016 | Feng | G06F 8/315 |
| 9,922,104 B1 * | 3/2018 | Kapoor | G06F 16/254 |
| 10,042,685 B1 * | 8/2018 | O'Kennedy | H04L 9/14 |
| 11,463,416 B1 * | 10/2022 | Ashman | H04L 67/133 |
| 2010/0106684 A1 * | 4/2010 | Pizzo | G06F 16/275 707/610 |
| 2014/0101676 A1 * | 4/2014 | Lovegrove | G06F 9/542 719/328 |

(Continued)

*Primary Examiner* — Alicia M Willoughby
(74) *Attorney, Agent, or Firm* — Steven Stupp

(57) ABSTRACT

A computer system that detects a change and automatically performs a remedial action associated with an application programming interface (API) for an application is described. During operation, the computer system may receive data from a second computer system that implements a data-query engine for a database and the data may be associated with the database. Then, the computer system may detect the change in the data based at least in part on one or more of: a schedule of when to check for the change; a location in the database associated with the data; expected content of the data; or a relationship between the data and additional data. When the change is detected, the computer system may perform the remedial action, where the remedial action includes providing a notification with information specifying a data element associated with the API that is affected by the change.

20 Claims, 10 Drawing Sheets

(56) References Cited

U.S. PATENT DOCUMENTS

| | | | | |
|---|---|---|---|---|
| 2016/0316016 A1* | 10/2016 | Arenas | ................... | H04L 67/01 |
| 2018/0089005 A1* | 3/2018 | Green | ................... | G06F 9/547 |
| 2018/0225732 A1* | 8/2018 | Doshi | ................. | G06Q 10/101 |
| 2019/0034199 A1* | 1/2019 | Pollock | ................... | G06F 8/73 |
| 2019/0034210 A1* | 1/2019 | Palladino | ................ | G06F 9/547 |
| 2019/0377989 A1* | 12/2019 | Dizengof | ................ | G06F 9/448 |
| 2020/0162516 A1* | 5/2020 | Israel | ................... | G06F 21/566 |
| 2020/0233787 A1* | 7/2020 | Battaglia | ............. | H04L 63/0876 |
| 2020/0351332 A1* | 11/2020 | Palladino | ............ | H04L 67/1004 |
| 2021/0048987 A1* | 2/2021 | Kedida | .................... | G06F 8/65 |
| 2021/0067337 A1* | 3/2021 | Bahrami | ................ | H04L 9/06 |
| 2021/0216288 A1* | 7/2021 | Bahrami | ............ | G06F 11/3688 |

\* cited by examiner

```
                                              ⸺ 400

┌─────────────────────────┐
            │   RECEIVE INFORMATION   │
            │           410           │
            └───────────┬─────────────┘
                        │
                        ▼
            ┌─────────────────────────┐
            │    AUTOMATICALLY AND    │
            │ DYNAMICALLY GENERATE AN API │
            │           412           │
            └───────────┬─────────────┘
                        │
                        ▼
            ┌─────────────────────────┐
            │ PERFORM ONE OR MORE     │
            │ ADDITIONAL OPERATIONS   │
            │      (OPTIONAL)         │
            │           416           │
            └─────────────────────────┘
```

MONITORING AND AUTOMATIC UPDATING OF AN APPLICATION PROGRAMMING INTERFACE

CROSS REFERENCE TO RELATED APPLICATIONS

This application is a continuation of U.S. patent application Ser. No. 17/344,663, "Dynamically Determining a Portion of a Database Schema," by Kristen Michelle Jones, filed on Jun. 10, 2021, which claims priority under 35 U.S.C. 119(e) to U.S. Provisional Application Ser. No. 63/038,349, entitled "Dynamically Determining a Portion of a Database Schema," by Kristen Michelle Jones, et al., filed on Jun. 12, 2020, the contents of both of which are herein incorporated by reference.

FIELD

The described embodiments relate to monitoring and automatic updating of an application programming interface (API).

BACKGROUND

In recent years, electronic health records (EHRs) have been widely adopted throughout the heath-care industry. EHRs allow hospital provider groups (HPGs) to electronically store and access patient data. In principle, using EHRs, HPGs can leverage patient data to improve patient outcomes, reduce costs, and provide improved services (e.g., by allowing patient data to be used in a wide range of new and existing applications). However, in practice, it has often proven difficult to leverage EHRs to achieve these goals. This is frustrating for HPGs, as well as their business partners and suppliers, and results in increased costs for payors and patients, as well as increased patient mortality and suffering.

SUMMARY

In a first group of embodiments, a computer system (which may include one or more computers) that dynamically determines a portion of a schema for a database is described. This computer system may include: a network interface that communicates with a second computer system that stores source code corresponding to the database; a processor that executes program instructions; and memory that stores the program instructions. During operation, the computer system may receive, at the network interface, an instruction to dynamically determine the portion of a schema of the database, where the instruction specifies a field in the database and the portion of the schema is initially unknown or unavailable to the computer system. Then, the computer system may determine the portion of the schema based at least in part on the instruction, where the determining includes interacting, via the network interface with the second computer system and interpreting the source code, and the portion of the schema includes information specifying the field and contents associated with the field. Next, the computer system may provide, from the network interface, the determined portion of the schema.

Note that the information may specify an interrelationship between the field and a second field in the database.

Moreover, the computer system and the second computer system are at different locations and/or may be associated with different organizations or entities.

Furthermore, the database may be associated with EHR software and may include patient medical data.

Additionally, the information specifying the field may include a name of the field. Moreover, the information may include a type of data. For example, the type of data may include an order type, such as: a medication order, a laboratory test, and/or a procedure order. In some embodiments, the information may include a format of the field.

Note that the contents may include a value associated with the field.

Moreover, the portion of the schema may not be stored by the computer system after the portion of the schema is determined.

Furthermore, the computer system may receive, from the network interface, a second instruction to dynamically determine a second portion of a schema of the database, where the instruction specifies a second field in the database and the second portion of the schema is initially unknown or unavailable to the computer system. Then, the computer system may determine the second portion of the schema based at least in part on the second instruction, where the determining comprises interacting, via the network interface with the second computer system and interpreting the source code, and the second portion of the schema may include second information specifying the second field and contents associated with the second field. Next, the computer system may provide, to the network interface, the determined second portion of the schema.

Additionally, the instruction may: be associated with a predefined schedule; be in response to an upgrade to the database; be in response to an error in an application that uses data associated with the field; be in response to an error in an API associated with the application; or occur when the API associated with the application is called.

Another embodiment provides a computer-readable storage medium for use with the computer system. When executed by the computer system, this computer-readable storage medium causes the computer system to perform at least some of the aforementioned operations.

Another embodiment provides a method, which may be performed by the computer system. This method includes at least some of the aforementioned operations.

In a second group of embodiments, a computer system (which may include one or more computers) that dynamically generates an API is described. This computer system may include: a network interface that communicates with a second computer system that implements a data-query engine for a database and a third computer system that implements an application; a processor that executes program instructions; and memory that stores the program instructions. During operation, the computer system may receive information that specifies an API configuration, where the API configuration includes second information specifying data associated with the database, and desired results of a query for the data that are used by the application. Then, the computer system may automatically and dynamically generate the API based at least in part on the API configuration, where the API is not specified using predefined or preprogramed software.

Note that the second information may include: third information specifying one or more fields in the database, constraints of the data, and/or a dynamic constraint that specifies one or more instances of the data in the database. For example, the constraints on the data may include: a type of the data, a format of the data, a range of values of the data, a patient identifier, a department identifier, an identifier of an organization, and/or an operational constraint. Moreover, the operational constraint may include: an inequality operation, an equality operation, an inclusion operation, an exclusion operation, a starting symbol, an end symbol, and/or a length operation. Furthermore, the constraints on the data may include: whether an ordered medication was picked up, whether an ordered procedure was performed, and/or or whether an ordered medical test was performed. Additionally, the third information may specify different fields in the database.

In some embodiments, the API may: provide, from the network interface and addressed to the second computer system, an instruction for the query for the data based at least in part on the second information; receive, at the network interface, results of the query associated with the second computer system, where the results comprise raw data; transform the raw data into the data based at least in part on the desired results; and provide the data. For example, the transformation may convert the raw data into a readable format for the third computer system. Moreover, the computer system may provide the data addressed to the third computer system.

Furthermore, receiving the information may include accessing the API configuration in the memory and/or receiving user-interface activity that specifies the API configuration. Additionally, the API configuration may correspond to natural language that is received by the computer system.

Additionally, the computer system may receive a request for the data associated with an application, and the API may be automatically and dynamically generated in response to the request.

In some embodiments, the API may be associated with an endpoint or address in the computer system that is common to multiple APIs.

Note that the API may include abstraction layers and configuration settings instead of the predefined or preprogramed software.

Moreover, the second computer system and/or the third computer system may be different from the computer system.

Another embodiment provides a computer-readable storage medium for use with the computer system. When executed by the computer system, this computer-readable storage medium causes the computer system to perform at least some of the aforementioned operations.

Another embodiment provides a method, which may be performed by the computer system. This method includes at least some of the aforementioned operations.

In a third group of embodiments, a computer system (which may include one or more computers) that provides raw data or data is described. This computer system may include: a network interface that communicates with a second computer system that implements an API and a third computer system that implements a database; a processor that executes program instructions; and memory that stores the program instructions. During operation, the computer system may receive, at the network interface and associated with the second computer system, an instruction, where the instruction include information specifying the data associated with the database and a dynamic constraint that specifies one or more instances of the data in the database. Then, the computer system may provide, from the network interface, a data query addressed to the third computer system, where the data query is based at least in part on the instruction. Moreover, the computer system may receive, at the network interface, results of the data query, where the results include the raw data corresponding to the data. Next, the computer system may provide, from the network interface, the raw data or the data addressed to the second computer system.

Note that the data query may specify one or more locations in the database.

Moreover, the data query may be based at least in part on a dynamic schema of a portion of the database. The portion of the schema of the database may not be stored in the computer system. Furthermore, the computer system may: provide, from the network interface and addressed to a fourth computer system, a request for the dynamic schema of the portion of the database based at least in part on the information; and receive, from the network interface and associated with the fourth computer system, the dynamic schema of the portion of the database.

Additionally, the dynamic constraint may include a patient identifier, a department identifier and/or an identifier of an organization.

In some embodiments, the computer system, the second computer system and the third computer system may be at different locations.

Moreover, the computer system and the third computer system may be associated with different organizations or entities. Alternatively, the computer system and the second computer system may be associated with a common organization or entity.

Note that the database may be associated with EHR software and may include patient medical data.

Another embodiment provides a computer-readable storage medium for use with the computer system. When executed by the computer system, this computer-readable storage medium causes the computer system to perform at least some of the aforementioned operations.

Another embodiment provides a method, which may be performed by the computer system. This method includes at least some of the aforementioned operations.

In a fourth group of embodiments, a computer system (which may include one or more computers) that detects a change and selectively performs a remedial action is described. This computer system may include: a network interface that communicates with a second computer system that implements a data-query engine for a database; a processor that executes program instructions; and memory that stores the program instructions. During operation, the computer system may receive, at the network interface, data associated with the second computer system and the database. Then, the computer system may detect the change in the data based at least in part on one or more of: a schedule of when to check for the change; a location in the database associated with the data; expected content of the data; or a relationship between the data and additional data. When the change is detected, the computer system may perform a remedial action, where the remedial action includes providing a notification with information specifying a data element associated with an API that is affected by the change.

Note that the location may be specified by a checksum associated with the data.

Moreover, the expected content and/or the relationship may indicate the change relative to expected values for the data.

Furthermore, the relationship may correspond to how the data is used by the API.

Additionally, the change may be detected based at least in part on one of: the API configuration, a security setting, and/or a transformation that converts raw data associated with the database into the data.

In some embodiments, the remedial action may include updating an API configuration. Moreover, the computer system may automatically and dynamically generate an updated API based at least in part on the updated API configuration.

Furthermore, the second computer system may be different from the computer system.

Additionally, the database may be associated with EHR software, and the database and the data may include patient medical data.

Another embodiment provides a computer-readable storage medium for use with the computer system. When executed by the computer system, this computer-readable storage medium causes the computer system to perform at least some of the aforementioned operations.

Another embodiment provides a method, which may be performed by the computer system. This method includes at least some of the aforementioned operations.

This Summary is provided for purposes of illustrating some exemplary embodiments, so as to provide a basic understanding of some aspects of the subject matter described herein. Accordingly, it will be appreciated that the above-described features are examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
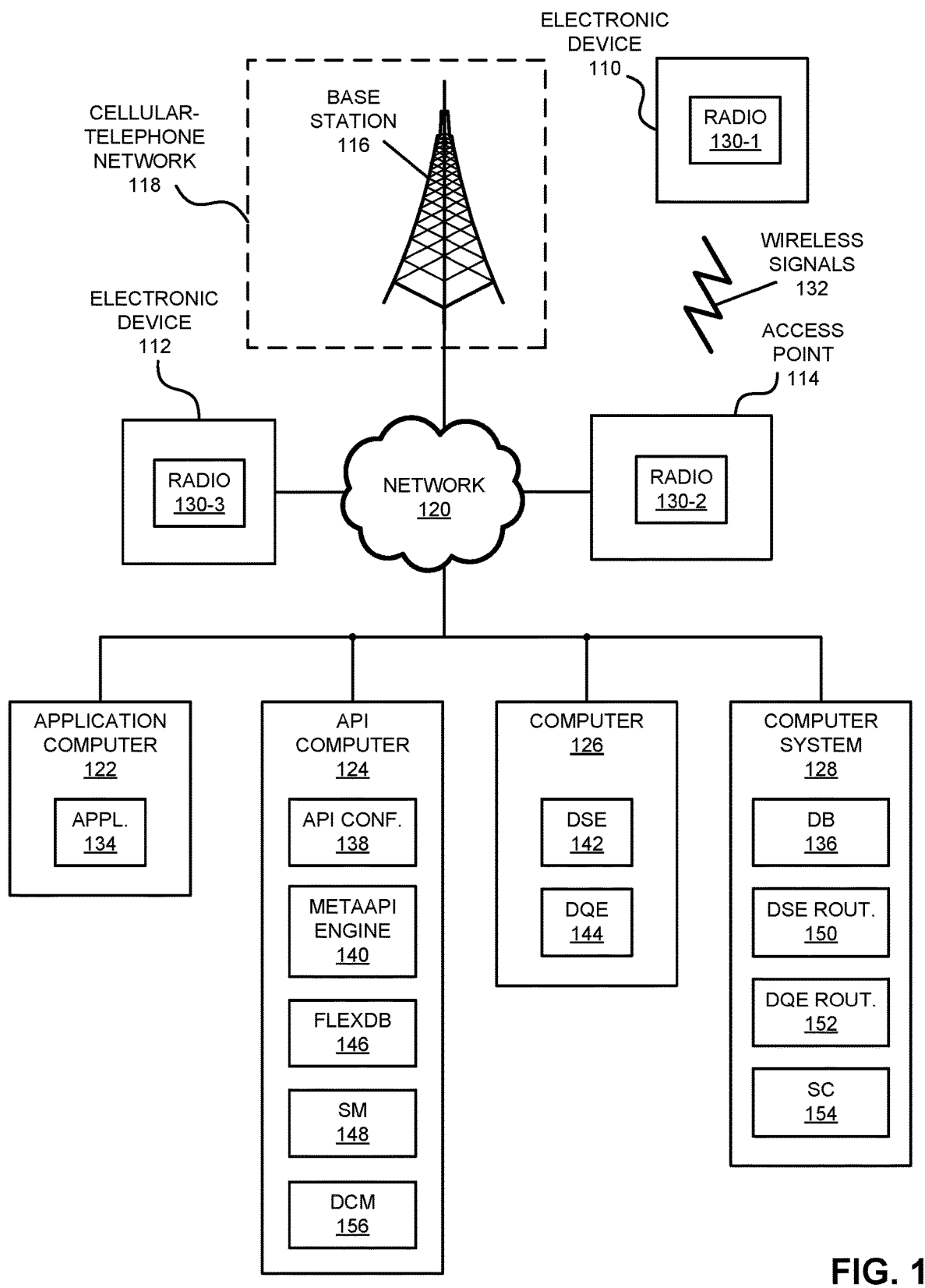
FIG. 1 is a block diagram illustrating an example of communication among electronic devices in accordance with an embodiment of the present disclosure.

In a first group of embodiments, a computer system that dynamically determines a portion of a schema for a database is described. During operation, the computer system may receive an instruction to dynamically determine the portion of a schema of the database, where the instruction specifies a field in the database and the portion of the schema is initially unknown or unavailable to the computer system. Then, the computer system may determine the portion of the schema based at least in part on the instruction, where the determining includes interacting with a second computer system that stores source code for the database and interpreting the source code, and the portion of the schema includes information specifying the field and contents associated with the field. Next, the computer system may provide the determined portion of the schema.

By facilitating the determination of an initially unknown or unavailable dynamic schema, these schema techniques allow the data fields and their interrelationships in the database to be used. For example, the portion of the schema may be used to create an API for an application, so that the application can interface with (e.g., access and obtain) data from the database. Moreover, the portion of the schema may be used to dynamically query data from the database. Consequently, the schema techniques may dynamically provide information that allows the data associated with the database to be used to provided value-added applications and services, which, in the context of healthcare, can enable improved outcomes and reduced costs.

In a second group of embodiments, a computer system that dynamically generates an API is described. During operation, the computer system may receive information that specifies an API configuration, where the API configuration includes second information specifying data associated with the database, and desired results of a query for the data that are used by the application. Then, the computer system may automatically and dynamically generate the API based at least in part on the API configuration, where the API is not specified using predefined or preprogramed software.

By dynamically generating the API, these generating techniques may facilitate improved operation of the application. For example, instead of using the predefined or preprogramed software, the API may be a codeless API that is flexibly adapted, as needed, to changes in the data and/or the database by updating the API configuration. This capability may reduce the time, effort and complexity of developing and/or maintaining the application and the API. Consequently, the generating techniques may facilitate value-added applications and services, which, in the context of healthcare, can enable improved outcomes and reduced costs.

In a third group of embodiments, a computer system that provides raw data or data is described. During operation, the computer system may receive an instruction from a second computer system, where the instruction include information specifying the data associated with a database and a dynamic constraint that specifies one or more instances of the data in a database. Then, the computer system may provide a data query to a third computer system that implements the database, where the data query is based at least in part on the instruction. Moreover, the computer system may receive results of the data query, where the results include the raw data corresponding to the data. Next, the computer system may provide the raw data or the data to the second computer system.

By providing the raw data or the data query, these query techniques may facilitate improved operation of an API, which may be implemented by the second computer system, and an application that communicates with the database via the API. For example, by separating the functions and operation of the computer system and the second computer system (and, thus, a data-query engine for the database and the API), the dynamic constraint may be separately updated, as needed, based at least in part on changes in the data and/or the database. This capability may reduce the time, effort and complexity of developing and/or maintaining the application and the API. Consequently, the query techniques may facilitate value-added applications and services, which, in the context of healthcare, can enable improved outcomes and reduced costs.

In a fourth group of embodiments, a computer system that detects a change and automatically performs a remedial action associated with an API for an application is described. During operation, the computer system may receive data from a second computer system that implements a data-query engine for a database and the data may be associated with the database. Then, the computer system may detect the change in the data based at least in part on one or more of: a schedule of when to check for the change; a location in the database associated with the data; expected content of the data; or a relationship between the data and additional data. When the change is detected, the computer system may perform the remedial action, where the remedial action includes providing a notification with information specifying a data element associated with the API that is affected by the change.

By detecting the change and automatically performing the remedial action, these monitoring techniques may facilitate improved operation of the API and an application that communicates with the database via the API. For example, the monitoring techniques may detect the change that would result in an error in the application and/or the API, and may either provide the notification with information that allows the change to be address or that automatically addresses the change by updating the API configuration (and, thus, the API). This capability may reduce the time, effort and complexity of maintaining the application and the API. Consequently, the monitoring technique may facilitate value-added applications and services, which, in the context of healthcare, can enable improved outcomes and reduced costs.

In the discussion that follows, one or more of the disclosed techniques may be used to access data (such as healthcare data) in real time (e.g., evaluating data of a patient who needs emergency department care to trigger a message) or not in real time (e.g., generating a quarterly quality of care report). Consequently, in the discussion that follows, data in an EHR (which is sometimes referred to as 'EHR data') is used as an illustrative example and may include or may be compatible with an EHR from: Epic Systems Corporation of Verona, Wisconsin; Cerner Corporation of North Kansas City, Missouri; MTBC, Inc. of Somerset, New Jersey; athenahealth of Watertown Massachusetts; GE Healthcare of Chicago Illinois; eClinicalWorks of Westborough, Massachusetts; NextGen Healthcare of Irvine, California; Allscripts Healthcare Solutions, Inc. of Chicago, Illinois; and/or another EHR vendor. However, in other embodiments the disclosed techniques may be adapted to an arbitrary source data system (and, thus, an arbitrary type of data and/or type of database, e.g., flat, hierarchical, relational, SQL-compliant, non-SQL, etc.), such as: enterprise resource planning (e.g., from Infor of New York City, New York), insurance claims data processing (e.g., Trizetto, Englewood, Colorado), human resources (e.g., from Oracle Corp. of Pleasanton, California), cost accounting (e.g., from EPSI of Chesterfield, Missouri), judicial (such as a court case management database), education (such as an education or a school database) and/or utilities (e.g., from Oracle Corp. of Pleasanton, California).

Note that, in the discussion that follows, an 'API' may be a software intermediary (a set of program instructions, routines, protocols, and/or tools) that allows different electronic devices or applications to exchange information with each other.

Moreover, an 'API configurator' may be a hardware and/or a software component that is used when an API is being created or updated. The API configurator may communicate with a dynamic schema engine (DSE) in real time, thereby enabling a user to view, as needed, a portion of the data schema, to select data fields, to define constraints for the data fields, and to update a customer-defined data model (which, as discussed further below, is sometimes referred to as a 'flexDB') and to deploy one or more configuration files via the DSE. The API configurator may be accessed by the user via a graphical user interface.

Furthermore, an 'API configuration' or an 'API configuration file' may be a file that contains parameters (such as text parameters) that define or specify settings or preferences for building or running a specific API, when referenced by a software program (such as an application).

Additionally, a 'business-to-business' (B2B) may be a company (such as a for-profit company) that provides data management, data analytic, digital application, and/or related services to HPGs and payers.

In some embodiments, a 'codeless API' or a 'no-code API' may use abstraction layers and configurations instead of a coded set of program instructions, routines, protocols, and/or tools for building software applications.

Moreover, a 'data order' may be the APIs that are associated with a single data use case.

Furthermore, a 'data query' may be a field-level request for data and/or metadata from a data source.

Additionally, a 'data use case' may be a specific situation or business purpose for which data is used (e.g., deciding if laboratory orders created for patients who sought care from an emergency department are appropriate).

In some embodiments, a 'dynamic query engine' (DQE) may be a hardware and/or a software component that is dynamically called by a codeless API to access data from a source system (such as a computer or a computer system that implements a type of database from a particular vendor, e.g., a particular EHR database) for use by an application.

Moreover, the DSE may be a hardware and/or a software component that is used when an API is being created and/or used to detect structural changes to items. When creating an API, the DSE may be called by the API configurator to dynamically reveal at least a portion of the schema of a database (such as source-system files of an HPG and/or data items through menus). In addition, the DSE may be called according to a schedule (e.g., once a day), on demand (e.g., after an EHR upgrade), in response to a trigger (e.g., when an application error occurs), and/or on the fly (e.g., when the API is called) to determine if data parameters of items called by the API have changed.

Furthermore, a 'fixed data model' may be a technique for data where the data elements are predefined or fixed. A data model may define or specify the logical inter-relationships and flow among specific data elements and the documentation of the way data are stored and retrieved. Note that a data model may represent what data are required and what format is to be used for different business processes. Business rules are often fixed in the structure of a data model, and small changes in the way business is conducted may result in large changes in computer systems and interfaces.

Additionally, a 'flexDB' may be a customer-defined data model that contains: a proxy (such as a checksum) for a schema that is built as data elements for use by an arbitrary API; information specifying where each item or field is used; one or more API configuration files; a security model and access; enhanced metadata, including naming conventions and transformation rules; concepts rules that map data elements that represent a concept (e.g., protected health information); and/or real-time detection of changes to data. A given customer may install an initial version of a flexDB that builds over time as new or modified APIs are defined.

In some embodiments, 'healthcare data' may encompass provider data that is siloed in EHR databases, imaging servers (e.g., MRI, X-ray), BLOB or document management servers (e.g., PDF, video, audio, pictures), and/or other clinical and operational data silos. More generally, healthcare data may include: patient-reported data, environmental data, one or more EHRs (such as social-demographic data, medical billing, diagnoses, visit summaries, laboratory results, prescriptions, procedures, in-patient medical records, healthcare-provider notes, etc.), medical test results, genetic data, etc.

Moreover, a 'HPG' may include a group of one or more providers that use the same instance(s) of an EHR system and that rely on the EHR system for storing other data.

Furthermore, a metaAPI engine' may include a hardware and/or a 'software' component that is called by an application to dynamically create a codeless API using one or more API configuration files stored in a flexDB of a customer.

Additionally, 'path-to-production' may include a sequence of phases and server environments through which software is tested and refined on its way to production for real-world use. Path-to-production often includes development, testing, and product environments. Note that software typically passes through quality gates in each phase of testing before it is permitted to progress to the next environment.

As discussed previously, it has often proven difficult to leverage EHRs to achieve goals, such as: improved patient outcomes, reduced costs, and/or improved services. Notably, HPGs typically control access to patient data and other types of data (which collectively are sometimes referred to as HPG data'). Indeed, getting access to HPG data as an internal customer (e.g., a Quality Care Department), a payor (such as a health-insurance company, a government agency, etc.), partner or a business-to-business vendor (such as a health information-technology or HIT vendor), typically involves considerable effort and time for the customers (either internal or external) and for HPGs to provide data integration and interoperability.

In order to access HPG data in real time, many HPGs use messages that are compatible with a Health Level Seven or HL7 standard (from Health Level Seven International of Ann Arbor, Michigan), which provides a set of rules that allow information to be shared and processed in a uniform and consistent manner. However, these rules are applied to HL7 messages by each organization in organization-specific code. Moreover, because HL7 allows for customization, there are often many variations and institution-specific modification to the HL7 standards. Consequently, there is not a single standard for how data is handled. Therefore, in order for applications to send and receive data they can understand, it is usually necessary for the data to be translated and/or mapped.

There are a variety of challenges and constraints to accessing HPG data using HL7 techniques, depending on the amount, transparency, and timing of the data access. Table 1 provides a summary of the challenges and constraints in using HL7 techniques to access HPG data.

TABLE 1

| Type of Problem | | HL7 Message | Data Fields | Reason for Problem | Data Issues Because of the Problem |
| --- | --- | --- | --- | --- | --- |
| What you get | Data bloat | On time | Contains too many data fields | HGPs usually do not want to create customized HL7 versions, so customers get the HL7 version that is already available, which often contains more fields than the customer needs | A customer often receives orders of magnitude more data than is being used by the application. This can stress system performance, including timeliness of response. It also puts the HPG at risk because more data than the customers need are outside the firewall. |
| | Data gaps | On time | Does not contain all required data fields | Only about 30% of HPG data are usually available via HL7 | A customer often must obtain data from batch files from the data warehouse. However, the data is at least 24 hours old |
| | Data distortions | One time | Contains all required data fields, but with transformations | Data are often transformed by rules based on previous requests, but these changes may not be documented | There is often no easy way to trace data linages, and support and change management are typically difficult |

TABLE 1-continued

| Type of Problem | | HL7 Message | Data Fields | Reason for Problem | Data Issues Because of the Problem |
|---|---|---|---|---|---|
| When you get it | Triggering issues | Late | Contains all required data fields | The HL7 transaction is often triggered too late | A customer often gets the data late and cannot use it for real-time transactions |
| | Queuing issues | Late | Contains all required data fields | The transaction often gets delayed in a queue | A customer often gets the data late and cannot use it for real-time transactions |
| | Missing transactions | Missing | N/A | About 5% of the time, HL7 transactions are not completed because of network blips, queuing issues, processing issues, etc. | There is often no notification that a message was not delivered, and the customer usually does not know data are missing until their users tell them |

While HL7 traditionally focused exclusively on integrating clinical applications (e.g., connecting one EHR to another), there is an increasing need in healthcare settings to access a much broader range of HPG data and to use nonclinical applications that need to access HPG data and that use modem technology approaches, such as APIs. APIs make it easy to provide HPG data to health-care providers and individuals on a wide variety of electronic devices (such as computers, cellular telephones). Moreover, APIs allow third-party application developers to provide medical applications that can be integrated into existing systems.

Consequently, Health Level Seven International has proposed Fast Healthcare Interoperability Resources (FHIR) standards that describe data formats and elements, and an API for exchanging HPG data. In terms of adoption, the FHIR standards for specific data elements are at different states of maturity (e.g., levels 0 to 6, where '6' is the most advanced state based at least in part on the type and level of review), but few of the resources are at a maturity level of '5' or above.

However, the use of APIs has many of the same challenges as HL7 integration. For example, APIs may not be interoperable if different versions of FHIR are implemented in different systems or when EHR vendors do not implement all available FHIR APIs or the entire API. More generally, the use of APIs alone does not really solve fundamental problems with accessing HPG data.

The work needed to implement an application that accesses and uses HPG data can typically be divided into three phases: initial mapping to access the data through implementation or go-live; tracking and identifying errors in an application, and figuring out the cause of the error; and fixing the error. The operations in these phases often require iterative and interdependent interaction of multiple parties at data requester (e.g., a HIT vendor or an internal customer) and the data owner (e.g., the HPG). Therefore, the data requester is usually dependent on availability of the HPG information-technology staff support. Moreover, the implementation phase may take several months and this work also usually involves changes to hardware and software infrastructure. Identifying and fixing errors typically involves many weeks of effort, which is often unscheduled and occurs repeatedly.

For example, after a HIT vendor signs a contract with an HPG, it often takes several months and tens of thousands of dollars to implement an application. There are multiple factors that impact the development time and the cost.

Notably, a data request from a HIT vendor may be mapped by the HPG to the relevant source system data fields. This process is iterative, and is typically uncertain and time-consuming, because the user is blind to the EHR database schema, which often varies from instance to instance even for the same EHR platform. For example, an EHR from one large EHR vendor has one file for all orders, and uses an opaque naming convention to distinguish order types (e.g., a laboratory order versus a medication order). Moreover, the user is also blind to other important information. Notably, a naïve user may not recognize that there are specific clinical order designations, such as, 'pending' versus 'resulted' status. Furthermore, the fields may vary between different installations of EHRs from this EHR vendor. Because HIT vendors have no visibility to EHR source data of an HPG, they usually work with HPG analysts, who differ substantially in their experience and knowledge of the source system data when translating a data request into an accurate mapping of the data fields used to create and meet the data-order requirements. This process of creating the correct data-order requirements is typically iterative and can take several months to complete.

Additionally, most HPGs operationalize access to their HPG data. Notably, after a HIT vendor has viewed a sample of the data, HPG developers create or customize the HL7 messages and/or APIs and make them available to the application from the HIT vendor. However, the customization is often delayed by months because it is usually added to the backlog of requests that the HPG is always working through.

Moreover, after the customization is completed, the HIT vendor may have to validate that the HPG data that is being accessed by their application through the HL7 messages and/or APIs is the correct data and that there is no unexpected data formats or missing data. Typically, before moving to a production environment, the HIT vendor first installs their application and data access code in a test environment. During this process, errors in the HPG data are invariably discovered, and the HL7 message and/or API code or software usually needs to be modified and retested. The effectiveness of testing at this point often largely depends on how robust the HPG data is in the source system test environment. If the test HPG data is an accurate replica of the production data, then variations in the HPG data may be discovered. Usually, however, the test HPG data is not robust and 'testing' typically continues in the production environment where new errors may occur because the amount of data and the variation of data are at their fullest.

Furthermore, in order to be accessed by users in live settings, the application from the HIT vendor needs to promoted to the production environment. Notably, the application and data access code need to be promoted to the source system production environment, which requires HPG approval and occurs on an HPG established and defined schedule. However, in the production environment, the application may break or fail because the HPG data that were used in the test environment were not sufficiently robust to test the data variation. Undetected variability in the HPG data is one cause of application failures that occur following implementation in the production environment. Consequently, the HPG data order often needs to be refined and the preceding operations in the path-to-production environment (such as identifying the source of data variability, updating the HL7 messages and/or API(s) code or software, retesting HL7 messages and/or API(s), promoting the application to the production environment, etc.) typically need to be repeated, which consumes valuable time.

After an application is successfully implemented, tested and promoted to the production environment, a HIT vendor often faces challenges in maintaining their application. Several of these problems for HL7 are summarized in Table 1. Even with APIs, there are usually still data-related challenges. Notably, errors may occur because the source data is typically changed from time to time, usually without notification or documentation. When a data element that is being used by an application is suddenly changed by the HPG (e.g., because of an EHR upgrade and/or a workflow change), it may cause the application to malfunction or stop working. When this occurs, the HPG may notify the HIT vendor that their application is not working and that it needs to be fixed. The burden of identifying and repairing the application usually falls on the HIT vendor (with limited assistance from information-technology resources at the HPG), because the HPG staff that notifies the HIT vendor of their application failure typically does not know the reason for the failure even when the failure was caused by a change to the HPG data made by the HPG. In addition to the time and effort needed to identify and fix the application, the HIT vendor usually needs to repeat the operations in the path-to-production environment to apply the HL7 messages and/or API fix. Consequently, there may be a significant time lag from error to fix, which may adversely impact user confidence in the application and the reputation of the HIT vendor.

Thus, HIT vendors typically face multiple business challenges in working with HPGs. Notably, after a HIT vendor gets an HPG customer to commit to an initial contract (e.g., for 12 months), it may take many months (e.g., six months) for the HIT vendor to install their software and several more months for them to work out the errors in the application. Consequently, there is often little time left for the HIT vendor to prove the value of their application, before they begin discussions for a contract renewal. Moreover, the HPG is often left wondering why the HIT vendor did not deliver value, especially given all of the effort they invested in installing the application.

Furthermore, if the HIT vendor gets a continuation of their contract with an HPG, they have to invest more in client support staff than expected because of the repeated and extensive break-fix cycle that they must go through. In general, as the number of HPG clients of a HIT vendor increases, there is an even larger increase in the number of data analyst, coding, and management staff to rapidly complete the break-fix cycle and to maintain their applications in production environments. This increasing overhead reduces profits and, thus, the ability of the HIT vendor to invest in product development. Stated differently, the existing application paradigm with HPGs does not scale.

Additionally, HIT vendors are often reluctant to update their applications. Notably, they do not know what other HPG data is currently available that could improve their products, and any changes to the applications could result in additional and costly break-fix cycles. Therefore, the existing application paradigm with HPGs discourages experimentation.

From the perspective of HPGs, the existing application paradigm poses several challenges in leveraging the value of the HPG data. Notably, the information technology department at an HPG may need to manage hundreds of applications and face an unending demand and backlog for user interfaces, reports, and HPG data requests from HIT vendors and internal users. Moreover, the information technology departments at HPGs are typically taxed by the labor costs of hard-to-find data analysts, developers, and other technical talent that install and maintain applications and that manage the work created by EHR enhancements and upgrades. However, in the process, internal customers are typically dissatisfied because of the long wait time to get information-technology-related work completed and the delays in being able to use innovative solutions.

Furthermore, HPGs are also often burdened with managing data security for their internal and external customers. Notably, customers that have HL7 or domain based-API access are often given access to file-level HPG data (e.g., a laboratory order file), even though their HPG data needs only include a subset of the fields from the file that is accessed. Consequently, an HPG may not know if the customer is only using approved HPG data, because more HPG data than needed are usually exposed outside of the HPG firewall.

Additionally, while HPGs spend a substantial amount of money on obtaining, managing, and securing their HPG data, they spend relatively little on actually using their HPG data. For example, while only a modest increase in spending would be required to hire the talent (e.g., statisticians, data scientists, informaticians, etc.) to maximize the value of the data assets of the HPGs, few HPGs make this investment because it is too hard to get access to the HPG data and too difficult to find the technical talent that can manage the process.

From the perspective of payors, the existing application paradigm also poses several challenges. Notably, payors increasingly have value-based contracts with HPGs. A typically contract usually requires access to HPG data for prior authorization, to evaluate quality of care, and/or to provide guidance. Consequently, a given contract often requires a collaboration, in which: a payor can access HPG data on patients who are payor members; process this HPG data against their analysis techniques; and return a recommendation for care or use the HPG data to evaluate performance. However, payors usually face the same challenges in accessing HPG data as everyone else, and often do not have the means to scale access across their many HPG customers. Moreover, in general, they face the same limitations as the HIT vendors and HPGs in terms of the time for implementation, data variation and HPG data changes, and the same constraints on innovation and modifying their analysis techniques. Furthermore, payors also face challenges in having a scalable way to communicate recommendations back to providers and to monitor subsequent actions taken.

In the discussion that follows, electronic devices may communicate packets or frames with wired and/or wireless networks (e.g., via access points, radio nodes or base stations) in accordance with a wired communication protocol (such as an Institute of Electrical and Electronics Engineers or IEEE 802.3 standard, which is sometimes referred to as 'Ethernet', or another type of wired interface) and/or a wireless communication protocol, such as: an IEEE 802.11 standard (which is sometimes referred to as 'Wi-Fi,' from the Wi-Fi Alliance of Austin, Texas), Bluetooth (from the Bluetooth Special Interest Group of Kirkland, Washington), a cellular-telephone communication protocol (such as 2G, 3G, 4G, 5G, Long Term Evolution or LTE, another cellular-telephone communication protocol, etc.) and/or another type of wireless interface. In the discussion that follows, Wi-Fi, a cellular-telephone communication protocol and Ethernet are used as illustrative examples. However, a wide variety of communication protocols (such as) may be used. Note that the wireless communication may occur in a variety of frequency bands, such as: a cellular-telephone communication band, a frequency band associated with a Citizens Band Radio Service, a Wi-Fi frequency band (such as a 2.4 GHz, a 5 GHz, 6 GHz and/or a 60 GHz frequency band), etc. In some embodiments, communication between electronic devices may use multi-user transmission (such as orthogonal frequency division multiple access or OFDMA).

FIG. 1 presents a block diagram illustrating an example of communication among one or more of electronic devices 110 and 112 (such as a cellular telephone, a computer, etc., and which are sometimes referred to as 'clients'), access point 114, base station 116 in cellular-telephone network 118, application computer 122, API computer 124, computer 126 (such as a Web server) and computer system 128 in accordance with some embodiments. Access point 114 and/or base station 116 may communicate with application computer 122, API computer 124, computer 126 and computer system 128 via network 120 (such as the Internet) using wireless and/or wired communication (such as by using Ethernet or a communication protocol that is compatible with Ethernet). Moreover, access point 114 and/or base station 116 may communicate with electronic device 110 using wireless communication (Wi-Fi and a cellular-telephone communication protocol, respectively), and may communicate with electronic device 112 via network 120 using wired communication. Note that access point 114 may include a physical access point and/or a virtual access point that is implemented in software in an environment of an electronic device or a computer. In some embodiments, API computer 124 and computer 126 may communicate using hypertext transfer protocol secure (HTTPS) representational state transfer (rest), and computer 126 and computer system 128 may communicate using transmission control protocol/Internet protocol (TCP/IP).

While not shown in FIG. 1, the wired and/or wireless communication with electronic devices 110 and/or 112 may further occur via an intra-net, a mesh network, point-to-point connections, etc., and may involve one or more routers and/or switches. Furthermore, the wireless communication may involve: transmitting advertising frames on wireless channels, detecting one another by scanning wireless channels, establishing connections (for example, by transmitting association or attach requests), and/or transmitting and receiving packets or frames (which may include the association requests and/or additional information as payloads). In some embodiments, the wired and/or wireless communication in FIG. 1 also involves the use of dedicated connections, such as via a peer-to-peer (P2P) communication technique.

Figure 10:
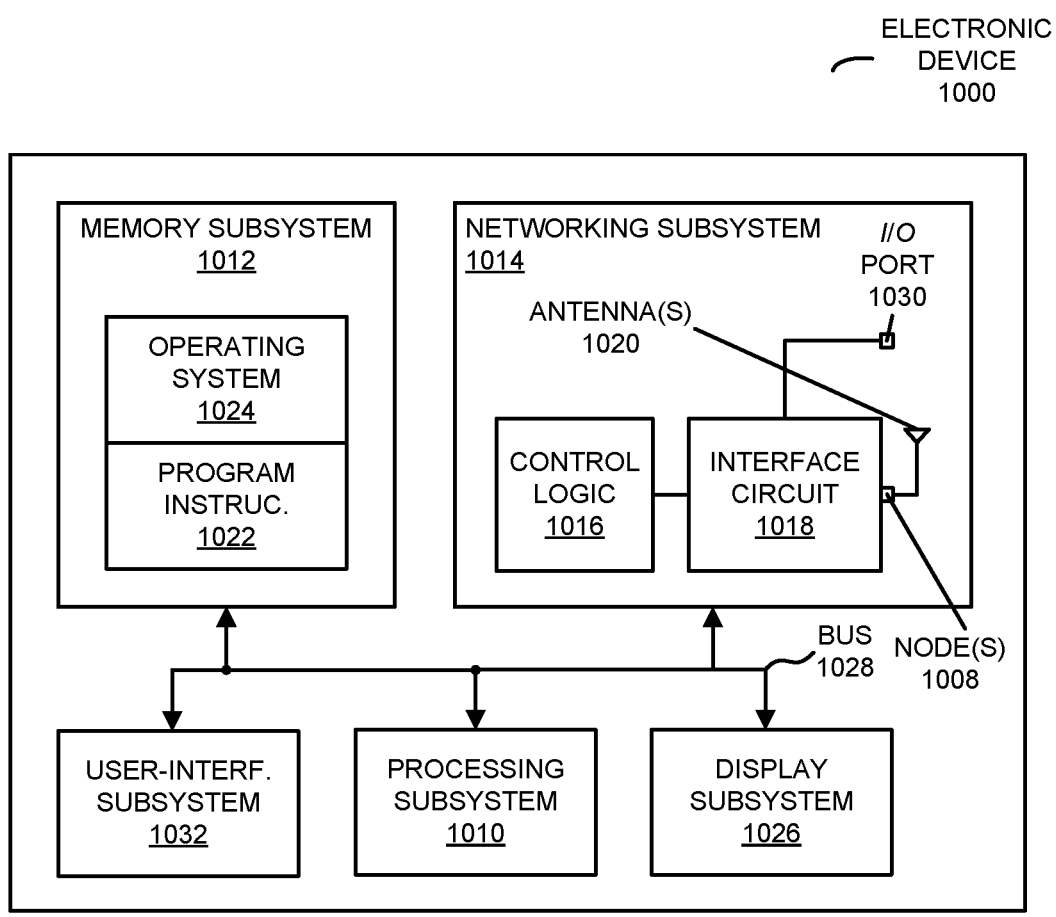
FIG. 10 is a block diagram illustrating an example of an electronic device in accordance with an embodiment of the present disclosure.

As described further below with reference to FIG. 10, electronic device 110, electronic device 112, access point 114, base station 116, application computer 122, API computer 124, computer 126 and/or computer system 128 may include subsystems, such as a networking subsystem, a memory subsystem and a processor subsystem. In addition, electronic device 110, access point 114 and base station 116 may include radios 130 in the networking subsystems. More generally, electronic device 110, electronic device 112 and access point 114 can include (or can be included within) any electronic devices with the networking subsystems that enable electronic device 110 and access point 114 to communicate with each other using wireless and/or wired communication. This wireless communication can comprise transmitting advertisements on wireless channels to enable access point 114 and/or electronic device 110 to make initial contact or detect each other, followed by exchanging subsequent data/management frames (such as association requests and responses) to establish a connection, configure security options (e.g., Internet Protocol Security), transmit and receive packets or frames via the connection, etc. Note that while instances of radios 130 are shown in electronic device 110 and access point 114, one or more of these instances may be different from the other instances of radios 130.

As can be seen in FIG. 1, wireless signals 132 (represented by a jagged line) are transmitted from radio 130-1 in electronic device 110. These wireless signals may be received by radio 130-2 in access point 114. Notably, electronic device 110 may transmit packets or frames. In turn, these packets or frames may be received by access point 114. Moreover, access point 114 may allow electronic device 110 to communicate with other electronic devices, computers and/or servers via network 120.

Note that the communication among components in FIG. 1 may be characterized by a variety of performance metrics, such as: a received signal strength (RSSI), a data rate, a data rate for successful communication (which is sometimes referred to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization').

In the described embodiments processing a packet or frame in electronic device 110 and/or access point 114 includes: receiving signals (such as wireless signals 132) with the packet or frame; decoding/extracting the packet or frame from received wireless signals 132 to acquire the packet or frame; and processing the packet or frame to determine information contained in the packet or frame. In some embodiments, communication between two or more electronic devices or components in FIG. 1 may be secure (such encrypted communication, a virtual private network, etc.).

Although we describe the network environment shown in FIG. 1 as an example, in alternative embodiments, different numbers or types of electronic devices may be present. For example, some embodiments comprise more or fewer electronic devices. As another example, in another embodiment, different electronic devices are transmitting and/or receiving packets or frames. Moreover, electronic devices and/or components in FIG. 1 may be implemented locally or remotely (e.g., API computer 124 and/or computer 126 may be cloud-based, or API computer 124 may be cloud-based and computer 126 may be included in an environment of an HPG along with computer system 128). Furthermore, functions of one or more components in FIG. 1 may be implemented by one or more electronic devices (such as in a distributed manner), and the one or more electronic devices may be at a single location or multiple locations. Alternatively, functions of two or more components in FIG. 1 may be combined and/or performed by a different component in FIG. 1.

As discussed previously, it can be challenging to implement and maintain an application 134 on application computer 122 that access data in a database (DB) 136 associated with computer system 128. For example, when there is a change in database 136, application 134 may no longer be interoperative or compatible with database 136. This may necessitate expensive diagnosing of one or more errors, repair and retesting of application 134, which may be time-consuming and expensive. In conjunction with the long lead time for implementing application 134, it can be difficult to leverage data in database 136.

As described further below with reference to FIGS. 2-9, in order to address these problems, one or more components in FIG. 1 may implement the schema techniques, the generating techniques, the query techniques and/or the monitoring techniques. For example, API configurator 138 and/or dynamic metaAPI engine 140 in API computer 124 may implement the generating techniques and/or the monitoring techniques. Moreover, DSE 142 in computer 126 may implement the schema techniques, and DQE 144 in computer 126 may implement the query techniques.

Notably, the disclosed techniques may allow a user to dynamically view a data domain-specific (e.g., laboratory results) representation of a schema of a source data system, such as of database 136 in computer system 128. For example, a user may interact with a user interface associated with API configurator 138 and may leverage a dynamic schema for at least a portion of database 136, which is provided by DSE 142, to select parameters for an API (which may be stored in flexDB 146) and/or a security module (SM) 148. Then, API configurator 138 may generate an API configuration based at least in part on the selected parameters. Moreover, metaAPI engine 140 may use this API configuration to automatically and dynamically generate a codeless API. Note that the API configuration may be created and/or modified, as needed, on the fly (e.g., improve application 134 with new data, adapt to data variation, etc.), in order to update the codeless API. Furthermore, application 134 may interact with the API to request data, via DQE 144 from database 136. In some embodiments, these components in FIG. 1 may be used, in the same way, by an arbitrary user, such as: an HPG internal user (e.g., information-technology staff), a payor, a HIT vendor, and/or another type of user.

We now describe these components and techniques in more detail. A user may access API configurator 138 via a user interface to select and/or to provide (e.g., using natural language) data fields and parameters to create one or more codeless APIs. This user interface may be used to select from individual data elements that have been previously approved by an HPG administrator via security module 148 (which may provide a secure field-level data control protocol). Note that the user-interface activity (such as selections made by the user) may be documented in flexDB 146. Alternatively or additionally, a user may pick data elements that are subsequently approved by the HPG administrator in order for one or more codeless APIs to be put into production. This approach may solve the problem of a user being dependent on an HPG data analyst to identify requirements for selection of specific data fields and for the transformation of the associated data.

API configurator 138 may dynamically communicate with DSE 142 and, as needed, DSE 142 may dynamically determine aspects of the dynamic schema of database 136, such as: file names, associated data-item or field names (such as content or one or more attributes for a field having an identifier), data-value names (such as a type of a value), relationships (such as one or more links to one or more other files), indexes (such as pointers to specific information), mappings (which may convert multiple data-item or field names into a single data-item or field name), metadata (such as a format, e.g., numerical, date, character, etc.) and/or other related information about fields in database 136. However, note that DSE 142 may not directly reveal the actual schema of database 136. Thus, there may not be a fixed or predefined data dictionary. Instead, DSE 142 may generate or create an intuitively labeled representation of the source system schema (e.g., using natural language) in real time as requested by the user of API configurator 138. Moreover, as the user selects data items, API configurator 138 may build one or more configuration files. When the user finishes selecting the data elements and parameters for application 134, API configurator 138 may check that the selected fields were approved before the associated one or more API configurations are available for testing and use.

(While the preceding discussion used user selections in the user interface of parameters for an API configuration (such as data elements), in other embodiments the user may use concepts (e.g., for laboratory test orders) that allows the user to select predefined fields related to a specific domain or concept. For example, a user may work at a concept level to specify (instead of the data requirements) and pull the values of the appropriate fields (such as by mapping the concepts to the corresponding fields). Alternatively, the user may select a predefined or predetermined template with predefined parameters (such as a template that is based at least in part on a user history of parameters that were selected for another API configuration and/or a template for one or more similar users). In some embodiments, a pre-trained machine-learning model (such as a classifier or a regression model that was trained using a supervised-learning technique) and/or a pretrained neural network may be used to assist the user in making selections and, thus, in specifying an API configuration.)

Note that DSE 142 may allow the user dynamic access to the entire backend of the database schema. However, in the disclosed techniques, the determined portion(s) of the schema of database 136 may not be stored outside of computer system 128. Consequently, determined portion(s) of the schema may not be fixed. Instead, DSE 142 may dynamically determine the portion(s) in real time, as needed.

Subsequently, when application 134 needs to access data in database 136, it may call metaAPI engine 140 and may pass parameters identifying or specifying the configuration file(s) that should be used. MetaAPI engine 140 may reference the appropriate configuration file(s), which may be stored in flexDB 146 to dynamically create a codeless API that then calls DQE 144. DQE 144 may retrieve the data from database 136 and may make the data accessible to application 134 for use. Note that metaAPI engine 140 and DQE 144 may execute according to the security parameters that were set by an HPG administrator, which may allow the data to be accessed at the field level. This field-level security control may provide an HPG a level of data security control that does not exist in existing data-access solutions for healthcare data.

In order to enable the aforementioned operations, an HPG may first install software components corresponding to DSE 142 and DQE 144 in computer system 128. In the discussion that follows, an enterprise EHR is used as a non-limiting illustration. However, as noted previously, the disclosed techniques may be used with a wide variety of source system data and types of databases.

Notably, an operator of database 136 (such as information technology staff of an HPG) may install DSE routine 150 and DQE routine 152 on computer system 128 (e.g., using installation scripts, which may be remote or on premise) and may configure a server or a computer in computer system 128. For example, the operator may install DSE and DQE routine codes into cache code libraries in an environment that is setup for custom cache code or into Cerner command line (CCL) libraries in an environment that is setup for custom CCL code. After installation, DSE 142 and DQE 144 in computer 126 may communicate with DSE routine 150 and DQE routine 152 in order to define performance parameters, such as throttling and time-outs. Moreover, after DSE routine 150 and DQE routine 152 are installed and configured, they can be accessed by an arbitrary user that has been granted permission by the HPG. Note that, during operation, DSE routine 150 may read source code (SC) 154 corresponding to database 136, and DQE routine 152 may access data in database 136.

While DSE routine 150 and DQE routine 152 are installed on computer system 128, the one or more API configurations that include the parameters for an API are not stored in the source system environment (i.e., computer system 128). Consequently, when a given API configuration needs to be updated, the updates does not need to pass through the EHR path-to-production, which allows changes to be made in real time and in a manner that does not require or rely on HPG resources (other than having an HPG administrator review and approve access to data elements that are requested by the user if these data elements were not previously approved).

Moreover, after DSE routine 150 and DQE routine 152 are installed on computer system 128, the HPG administrator may use security module 148 (e.g., via a user interface) to set access approvals for one or more users or one or more subsets of users (e.g., HPG information-technology staff), and the HPG administrator may modify these approvals as needed. Security module 148 may be used by the HPG administrator to review and approve access to data requested by a user if the data to be accessed is outside of the more general approval parameters. Thus, by using the disclosed techniques, the HPG administrator may set and audit field-level security for the given user. For example, vendors may no longer need to interact with an HPG data analyst or a developer. Therefore, this approach may bridge the divide that users face when they are blind to knowledge about the data. Consequently, in the disclosed techniques, a primary role of the HPG may be to provision data security, which is a benefit to the user (e.g., it may control the pace of work) and to the HPG (e.g., there may not be technical labor costs). While security module 148 is shown in API computer 124, in other embodiments it may be included in computer system 128.

As discussed previously, via a user interface, a user may dynamically access DSE 142 and flexDB 146 in order to view at least portions of the schema of database 136, and to build API configurations that define API parameters specific to the data that will be accessed. Moreover, as discussed previously, DSE 142 may dynamically reveals menu and user-driven representations of at least portions of the schema of database 136. Notably, the user interface may allow a user to display data-file names, data-item or field names, and data-values types in computer system 128, and to use a flexible data model to build an API configuration.

By being called in real time, DSE 142 may avoid challenges associated with existing approaches for accessing database 136. For example, one existing approach gives users menu-driven access to a database schema by copying or scraping selected features of the schema and providing a static representation of database 136 as it existed at the time of scraping. This existing approach is analogous to having a structured digital dictionary of the available data, which may work if the structure of a database does not change or if changes are only made on a defined schedule. However, EHR data fields in database 136 and even file structures may change from time to time, and a static representation of the schema may quickly become out of date. Moreover, creating a periodic updated representation of the entire schema of database 136 may involve substantial and unnecessary processing, because database 136 may be very large and many of the data fields may not be active. Furthermore, creating a direct representation of the schema of database 136 may be contrary to best practice and/or may not be allowed by a provider of database 136.

In order to select API data parameters, the user may: define a query, select results, and deploy the API. Notably, query parameters may be defined by specifying data requirements. For example, the user may select parameters that define the context (e.g., encounters in specific departments) and/or other constraints (e.g., patients who have a specific type of order) that define the healthcare relevant conditions for accessing the data. API configurator 138 may then dynamically build the API configuration as data fields for the parameters are selected and stored in flexDB 146. In some embodiments, the user may assemble combinations of parameters to define the conditions under which data are to be accessed. Next, DSE 142 may use information (such as metadata) associated with the data to reveal existing relationships among files through items, and this information may be accessed via the user interface associated with API configurator 138.

Furthermore, building a query with one or more parameters may follow a logical flow. For example, the user may view and select a 'file' option in a menu in the user interface. Then, the user may view and select: an item or field associated with the selected file, and/or one or more values associated with the selected item or field. Next, a parameter may be built after a file, item or field, and one or more values are selected. In some embodiments, the user may link multiple parameters in order to build a full query.

Note that a 'file' may represent one or more categories of elements, such as orders, encounters, and/or departments. When the file menu is selected in the user interface associated with API configurator 138, DSE 142 may reveal a list of available files that the user may select as the file (e.g., orders). Moreover, after a file has been selected (e.g., orders), another menu may indicate related items. These items may be associated with or specific to the parent file. For example, if the user selects 'orders' from the file menu, DSE 142 may then reveal or indicate a list of related items that may include: an order identifier, an order type, an order display name, an order date, an ordering provider identifier, an order description, a result date, etc.

Additionally, after an item or field has been selected (e.g., order type), an additional menu may reveal or indicate related values. These values may be associated with or specific to the parent item or field. For example, if the user selects 'order types' from the item or field menu, DSE 142 may then reveal or indicate a list of related values that may include: laboratory tests, medications, procedures, etc.

In some embodiments, the user may access logical options (e.g., AND, OR, NAND, NOR, XOR, another Boolean operation, etc.) to link parameters and to define an inclusion criterion for the query (such as an adherence rule, e.g., an ordered medication was picked up). Table 2 provides an example of a query that includes or is specified using five parameters.

TABLE 2 for all open laboratory test order for patients in the emergency department
orders (file) where the order type (field) equals (operator) lab (value)
AND (logic)
orders (file) where the order status (field) equals (operator) pending (value)
AND (logic)
encounters (file) where the patient identifier (field) equals (operator) order patient identifier (value)
AND (logic)
department (file) where department identifier (field) equals (operator) encounter department identifier (value)
AND (logic)
department (file) where department name (field) contains (operator) "Emergency Department" "Emerg Dept" "ED" (value)

In some embodiments, the file names provided by DSE 142 may be intuitively interpretable, so that users may select options without the need to view a reference guide for the EHR or may not need to consult with an experienced data analyst. Thus, DSE 142 may create at least a portion of the schema that is distinct and separate from the schema for database 136, where intuitive labels may be stored in a general (not customer-specific) flexDB to replace ambiguous or opaque codes that are often used by EHR vendors. Alternatively or additionally, DSE 142 may relabel or create metadata for at least a portion of the schama. In either of these contexts, note that flexDB 146 may be an EHR-specific instance asset that is a cumulative source of useable data intelligence that builds with each API that is created. In the process, a growing volume of reusable metadata (e.g., item or field or value-specific labels, help text, transformation rules, etc.) may be added to the general flexDB in order to reduce work for future requests and to standardize data. Overtime, a provider of components (such as one or more software modules or program instructions) associated with the described embodiments may amass a multi-instance view of instances of flexDBs that may be leveraged in order to enhance the options that HPGs may choose from when installing software modules and program instructions associated with the described embodiments. Note that, as flexDB 146 grows, API configurator 138 may first dynamically access its relevant metadata and then may refer to DSE 142.

After defining the query parameters, the user may then select specific data fields that will be returned when the codeless API is called. Note that when data elements are selected, API configurator 138 may dynamically update an API configuration file in flexDB 146.

For example, for the patients who meet the parameters defined in the 'data query' example, the user may select the files, items and values used to obtain an attending provider name (result) and the patient room number (result) for their response data. The user may have prior HPG administrator approval for these items, but the user may also select items for which they do not yet have approval. When this occurs, API configurator 138 may indicate that permission has not yet been granted by the HPG, and may send a request to a security queue for the HPG Administrator to review. Moreover, API configurator 138 may allow the users to build API configuration(s), but to automatically block access to the data until permission has been granted.

After the data fields have been selected, the user can apply one or more transformation rules to format a given field. Notably, raw data may be messy, formatted in ways that are hard to use, etc. Details on the transformation(s) are described further below. Briefly, the user may impose one or more transformation rules in order to strip away unnecessary content and/or in order to reformat the data so that it may be used by their application. Moreover, after the one or more transformation rules for the data fields are defined, they may then be saved in flexDB 146. These data-field specific transformation rules may be subsequently accessed in real-time by the API to access data. Furthermore, the same data-field specific metadata may also be selected as a single rule set when selecting data fields to create an API in the future. Note that the one or more transformation rules that are available may be generic or source-specific, such as specific to a particular instance of a database (such as database 136).

After the parameters have been defined, the data field has been selected and one or more transformation rules have been applied, the user may select a deploy option in this user interface that triggers a quality assurance review by security module 148 that checks for security approval (e.g., what items have been approved by the HPG administrator) and performance best practices. Then, if access to the selected items have been approved, metaAPI engine 140 may access the one or more API configurations that have been created, so that they can be tested and used in production by application 134. Alternatively, if access to the selected items has not been approved, a message may be sent to the HPG administrator by security module 148. In these embodiments, when access to the selected items is subsequently approved, metaAPI engine 140 may access the one or more API configurations, so that they can be tested and used in production by application 134.

The process up to this point in the preceding embodiments is user controlled and driven. Notably, the user may interact with the user interface associated with API configurator 138 to choose the files, data fields, the data parameters (such as items, values or attributes, identifiers for relationships, a wildcard parameter, and/or one or more operators, e.g., equals, does not equal, exists, does not exist, greater than, less than, contains, does not contain, starts with, ends with, a length, etc.), query constraints, the field-specific data transformations required for their application, change detection rules, and triggers for running the codeless API specified by one or more API configurations (or API configuration files). The one or more API configurations may be stored in flexDB 146. Note that if there is a need to modify the data request, the user may use API configurator 138 to make the changes and the corresponding API configuration may be dynamically modified. Table 3 provides an example of an API configuration for an application that uses laboratory test results, and where the API configuration is associated with a particular type of EHR database.

TABLE 3

```
{
   "configurationID" : "4",
   "parameters" : [
      {
         "name" : "departmentID",
         "type" : "string"
      },
      {
         "name" : "date",
         "type" : "string"
      }
   ],
   "tablefile" : "patient",
   "constraints" : [
      {
         "field" : "18880",
         "operator" : "1",
         "value" : "*departmentID*".
         "link" : "0",
         "history" : "Keep",
         "array" : "All",
         "logic" : "(",
         "status" : "0"
      },
      {
         "field" : "18855",
         "operator" : "4",
         "value" : "",
         "link" : "0",
         "history" : "Use",
         "array" : "All",
         "logic" : "and",
         "status" : "0"
      },
      {
         "field" : "18880",
         "operator" : "1",
         "value" : "*departmentID*".
         "link" : "0",
         "history" : "Keep",
         "array" : "All",
         "logic" : ") or (",
         "status" : "0"
      },
      {
         "field" : "18855",
         "operator" : "8",
         "value" : "*date*"
         "link" : "0",
         "history" : "Use",
         "array" : "All",
         "logic" : "and",
         "status" : "0"
      },
      {
         "field" : "210",
         "operator" : "3"
         "value" : "",
         "link" : "2=orders".
         "history" : "All",
         "array" : "All",
         "logic" : "B-link",
         "status" : "0"
      },
      {
         "field" : "30",
         "operator" : "1",
         "value" : "7",
         "link" : "0",
```

TABLE 3-continued

```
        "history" : "All",
        "array" : "All",
        "logic" : "and",
        "status" : "0",
      }
],
"reportList" :
"225>4001,210>*3*<2060>2061,226,226<8>10110,226<8>18884,
226<8>18882,225>.2[225>101],225>101[225>101],225>4001,226<8>18875,
226<8>18864,.1,90,34140,95000,100[34030],3000[34030],34030[34030],
205,1050,31,30,40>2000,40>.2,31,115,120,180,341,52928[34510],
34520[34510],34510[34510],305,310,330,335,28,1511,226<8>10110[10110]",
"response Translation" : {
"recordsObjectName" : "orders",
    "idName" : "orderID",
"nameName" : "0",
"DbName" : "0",
    "statusName" : "0",
"fieldsHandling" : "2",
"fieldsName" : ""
"fields" : [{
        "fieldNumber" : "225>4001",
        "fieldHandling" : "2",
        "fieldName" : "hospital",
    },{
        "fieldNumber" : "210>*3*<2060>2061",
        "fieldHandling" : "2",
        "fieldName" : "patientID1",
    },{
        "fieldNumber" : "226",
        "fieldHandling" : "2",
        "fieldName" : "patientID2",
    },{
        "fieldNumber" : "226<8>10110",
        "fieldHandling" : "2",
        "fieldName" : "patient_class",
        },{
"fieldNumber" : "226<8>18884",
        "fieldHandling" : "2",
        "FieldName" : "current_location_room",
        },{
"fieldNumber" : "226<8>18882",
        "fieldHandling" : "2",
        "FieldName" : "current_location_bed",
        },{
"fieldNumber" : "225>101",
        "fieldHandling" : "2",
        "FieldName" : "current_location_department",
        },{
"fieldNumber" : "4001",
        "fieldHandling" : "2",
        "FieldName" : "current_location_facility",
        },{
"fieldNumber" : "226<8>18875",
        "fieldHandling" : "2",
        "FieldName" : "admission_type",
        },{
"fieldNumber" : "226<8>18864",
        "fieldHandling" : "2",
        "FieldName" : " attending_physician ",
        },{
"fieldNumber" : ".1",
        "fieldHandling" : "2",
        "FieldName" : "order_number",
        },{
"fieldNumber" : "90",
        "fieldHandling" : "2",
        "FieldName" : "order_status",
        },{
"fieldNumber" : "95000",
        "fieldHandling" : "2",
        "FieldName" : "order_last_update",
        },{
"fieldNumber" : "34030",
        "fieldHandling" : "2",
        "FieldName" : "ordering_provider_id",
        },{
"fieldNumber" : "205",
        "fieldHandling" : "2",
        "FieldName" : "ordering_user_location",
```

TABLE 3-continued

```
     },{
"fieldNumber" : "1050",
     "fieldHandling" : "2",
     "FieldName" : "laboratory_name",
     },{
"fieldNumber" : "31",
     "fieldHandling" : "2",
     "FieldName" : "order_effective_time",
     },{
"fieldNumber" : "30",
     "fieldHandling" : "2",
     "FieldName" : "order_type",
     },{
"fieldNumber" : "40>2000",
     "fieldHandling" : "2",
     "FieldName" : "order_catalog_id",
     },{
"fieldNumber" : "40>.2",
     "fieldHandling" : "2",
     "FieldName" : "order_catalog_name",
     },{
"fieldNumber" : "115",
     "fieldHandling" : "2",
     "fieldFieldName" : "result_status",
     },{
"fieldNumber" : "120",
     "fieldHandling" : "2",
     "FieldName" : "order_priority",
     },{
     "fieldNumber" : "180",
     "fieldHandling" : "2",
     "FieldName" : "order_reason,
     },{
"fieldNumber" : "341",
     "fieldHandling" : "2",
  "FieldName" : "order_collector",
     },{
"fieldNumber" : "34510",
     "fieldHandling" : "2",
     "FieldName" : "scheduled_time",
     },{
"fieldNumber" : "305",
     "fieldHandling" : "2",
     "FieldName" : "collection_date",
     },{
"fieldNumber" : "310",
     "fieldHandling" : "2",
     "FieldName" : "collection_time",
     },{
"fieldNumber" : "330",
     "fieldHandling" : "2",
     "fieldFieldName" : "received_date",
     },{
"fieldNumber" : "335",
     "fieldHandling" : "2",
     "FieldName" : "received_time",
     },{
"fieldNumber" : "28",
     "fieldHandling" : "2",
     "fieldFieldName" : "results_available_time",
     }
  ]
}
}
```

Next, metaAPI engine 140 may dynamically generate the codeless API from the one or more API configurations, and metaAPI engine 140 may communicate with application 134 and DQE 144 to manage API calls. These operations may include: application 134 may provide a user call to metaAPI engine 140 with a name or identifier of the codeless API and API data parameters associated with requested data; in response metaAPI engine 140 may prepare a DQE call, and then DQE inputs in the DQE call may be submitted to DQE 144; DQE 144 may provide the DQE inputs to DQE routine 152 in computer system 128, which obtains the data from database 136; DQE routine 152 may provide raw data to DQE 144 (such as in a JavaScript object notation or JSON response); DQE 144 may provide the raw data to metaAPI engine 140 (e.g., in the JSON response); metaAPI engine 140 may perform a translation of the returned raw data into the data (e.g., into a readable JSON format, a natural language format, etc.), and then may provide the data to application 134 (e.g., in a formatted JSON response). Moreover, preparing the DQE call may include: fetching an API definition, validating API parameter inputs, standardizing the API definition into the DQE inputs, and/or calling one or more DQE endpoints. When preparing the DQE call, metaAPI engine 140 may interact with application 134, flexDB 146 and/or one or more API configurations. Note that operation of the codeless API may involve metaAPI engine 140 and DQE 144: metaAPI engine 140 may generate the codeless API, and DQE 144 may fulfill the DQE call or request.

Thus, in overview, when application 134 wants data, it may provide a user call to metaAPI engine 140. This user call may be initiated in real time, based at least in part on a predefined schedule (e.g., every 10 minutes), and/or in response to an occurrence of an event (e.g., a patient record is opened for an encounter, a medication is ordered, etc.) that results in a trigger for application 134.

When triggered, application 134 may call and passes information (e.g., the name of the codeless API, the API identifier, and the API data parameters) to metaAPI engine 140. Table 4 provides an example of a user call to the codeless API specified by the API configuration shown in Table 3.

TABLE 4

Request to MetaAPI Engine:
{
  "ConfigurationID" : "4",
  "departmentID" : "420008",
  "date" : "today"
} returned. For example, a request sent to metaAPI engine 140 may include a parameter for a department identifier (ID). This parameter may be a dynamic field, which means that a specific value needs to be added to the request sent to metaAPI engine 140 or it may be left blank in order to obtain information for all departments. In this example, the value is an identifier for a specific department, such as the emergency department.

After metaAPI engine 140 obtains or accesses the associated API configuration, it may validate that the number and type of parameters sent in the request from application 134 match what is in the associated API configuration. For example, metaAPI engine 140 may check that application 134 sent the correct two parameters for 'configuration ID 4.' If the number and type of parameters cannot be validated, then metaAPI engine 140 may send an error message back to application 134.

After validation, in order to standardize the API definitions into DQE inputs, the data request from application 134 may need to be translated from the user-friendly terms used in API configurator 138 back to the source system language, so DQE 144 can access the correct data. Table 5 provides an example, of the DQE inputs sent to DQE 144 for the user call or request shown in Table 4. This example illustrates the standardization when moving from the codeless API definitions in the API configuration shown in Table 3 as modified by the parameters in the user call or request shown in Table 4.

TABLE 5

Request to DQE:
Query String Parameters:
tablefile: patient
constraintList:
18880^1^420008^0^Keep^All^(^0|18855^4^^0^Use^All^and^0|
18880^1^420008^0^Keep^All^) or (^0|18855^8^64971^0^Use^All^and^0|
210^3^^2=order^All^All^B-link^0|30^1^7^0^All^All^and^0
reportList:
225>4001,210>*3*<2060>2061,226,226<8>10110,226<8>18884,226<8>18882,225>101,
225>.2,225>4001[4001],226<8>18875,226<8>18864,.1,90,34140,95000,100[34030],3000
[34030],
34030[34030],205,1050,31,30,40>2000,40>.2,31,115,120,180,341,52928[34510],34520
[34510],34510[34510],305,310,330,335,28,1511,226<8>10110[10110]
timeOut: 30

In response, metaAPI engine 140 may: select the corresponding one or more API configurations, validate that the inputs match what is required by the one or more API configurations, standardize the request to match the format required for the DQE inputs, and/or pass the DQE inputs to DQE 144. Then, DQE 144 may retrieve the requested data and send the response back to metaAPI engine 140, which translates the raw data response into, e.g., a JSON readable form before passing it back to application 134.

We now describe the operations associated with metaAPI engine 140 in more detail. Notably, in response to a user call for data, metaAPI engine 140 may fetch the API definition. For example, metaAPI engine 140 may use the configuration identifier sent by application 134 (see, e.g., Table 4) to access the associated API configuration(s) from flexDB 146. If the configuration identifier cannot be found, metaAPI engine 140 may send an error message back to application 134. Alternatively, if the API configuration(s) are found, then the parameters (such as those shown in Table 4) may be validated.

Note that a given API configuration may include parameters that need to be populated so that metaAPI engine 140 can send the request to DQE 144 and get the correct data Next, metaAPI engine 140 may call one or more DQE endpoints. Notably, after the API definitions are standardized into DQE inputs, metaAPI engine 140 may call and send the DQE inputs to a DQE endpoint (as shown, e.g., in Table 5). The DQE endpoint may be configurable and may be driven by the implementation for API access by computer system 128 and, thus, the HPG (e.g., directly to the on-premise source system, via an API gateway, etc.). DQE 144 may use the data field and logic inputs to execute the logic and return the raw data response to metaAPI engine 140.

Note that DQE 144 may be able to handle a wide variety of possible permutation of the DQE inputs because: the logic of the target data fields may be abstracted out of the source system DQE routine 152 (or code) and into the metaAPI configuration; DQE 144 may accept DQE inputs generated for an arbitrary application and then may execute them; and/or DQE 144 may be a hyper-variable, hyper-parametrized query engine.

Thus, DQE 144 may support a many-to-one embodiment, while existing approaches code the parameter names into a source query are typically based at least in part on a one-to-one relationship between a source system query and a given API. For example, if the user wanted laboratory test results, radiology, medications (or prescriptions) and encounters (such as office visits), they would usually need four source system query programs in the existing approaches, one for each of data type. In the disclosed techniques, the user may have four API configurations and one source system query program, DQE 144.

After receiving the raw data in the response, it may be transformed into a readable (user friendly) format, e.g., by DQE 144 and/or metaAPI engine 140. Notably, a given database system may have a default way of providing raw data output. While SQL systems are typically more standardized, not all databases are SQL-based (i.e., there are many other types of databases). Table 6 provides a truncated example of the raw response from an InterSystems cache database (from InterSystems of Cambridge, Massachusetts) in response to the DQE inputs shown in Table 5.

TABLE 6

...{"searchID":"70813041","processID":"7081304","status":"Complete","error":null,"percent": null,"perfCount":":.492191^151610^.14178","recordCount":"278","tablefile":"orders","page":"", "option":null,"records":[{"id":"334832334","name":"","Db":"","status":"Active","fields": [{"field":".1","history":[{"history":null,"array":["1"],"values":["334832334"]}]},{"field":"30", "history":[{"history":null,"array":["1"],"values":["Lab
[7]"]}]},{"field":"31","history":[{"history":null,"array":["1"],"values":["5562464548
[4/7/2017 09:02:28]"]}]},{"field":"90",
"history":[{"history":null,"array":["1"],"values":["Completed
[5]"]}]},{"field":"115","history":[{"history":"04/07/2017","array":["1"],"values":["Final
result[3]"]}]},{"field":"120",
"history":[{"history":null,"array":["1"],"values":["Routine
[6]"]}]},{"field":"205","history":[{"history":null,"array":["1"],"values":["SY UMP FAMILY
MED
[91001]"]}]},{"field":"226","history":[{"history":null,"array":["1"],"values":["154805467"]}]},
{"field":"305","history":[{"history":null,"array":["1"],"values":["64370[3/28/2017]"]}]},
{"field":"34030","history":[{"history":null,"array":["1"],"values":["ZZREHEARSAL, BOB
[900900]"]}]},{"field":"95000","history":[{"history":null,"array":["1"],"values":["5562464600
[4/7/2017
09:03:20]"]}]},{"field":"210>*3*<2060>2061","history":[{"history":null,"array":["2"],"values":
["0060397658"]}]},{"field":"225>4001","history":[{"history":null,"array":["1"],
"values":["ACME CLINICS ANDOVER
[7010]"]}]},{"field":"40>.2","history":[{"history":null,"array":["1"],"values":
["CARBAMAZEPINE
TOTAL"]}]},{"field":"40>2000","history":[{"history":"08/30/2016","array":["1"],"values":
["LAB21"]}]}]},{"id":"334832341","name":"","cid":"","status":"Active","fields":[{"field":".1",
"history":[{"history":null,"array":["1"],"values":["334832341"]}]},{"field":"30","history":
[{"history":null,"array":["1"],"values":["Lab
[7]"]}]},{"field":"31","history":[{"history":null,"array":["1"],"values":["5564296011
[4/28/2017
13:46:51]"]}]},{"field":"90","history":[{"history":null,"array":["1"],"values":["Completed
[5]"]}]},{"field":"120","history":[{"history":null,"array":["1"],"values":["Routine
[6]"]}]},{"field":"205","history":[{"history":null,"array":["1"],"values":["FAMILY MED
[950030]"]}]},{"field":"226","history":[{"history":null,"array":["1"],"values":["154806500"]
}]},{"field":"34030","history":[{"history":null,"array":["1"],"values":["ZZREHEARSAL,
OSWALD
[900902]"]}]},{"field":"95000","history":[{"history":null,"array":["1"],"values":["5564296011
[4/28/2017
13:46:51]"]}]},{"field":"210>*3*<2060>2061","history":[{"history":null,"array":["2"],
"values":["0060397658"]}]},{"field":"225>4001","history":[{"history":null,"array":["1"],
"values":["ACME CLINICS BLOOMINGTON OXBORO
[5340]"]}]},{"field":"40>.2","history":[{"history":null,"array":["1"],"values":["C.
DIFFICILE TOXIN BY PCR
(ACME)"]}]},{"field":"40>2000","history":[{"history":"11/05/2012","array":["1"],"values":
["LAB60080"]}]}]},{"id":"334832441","name":"","cid":"","status":"Active","fields":
[{"field":".1",
"history":[{"history":null,"array":["1"],"values":["334832441"]}]},{"field":"28","history":
[{"history":"03/21/2017","array":["1"],"values":["35640 [09:54:00]"]}]},{"field":"30",
"history":[{"history":null,"array":["1"],"values":["Lab
[7]"]}]},{"field":"31","history":[{"history":null,"array":["1"],"values":["5560998833
[3/21/2017 09:53:53]"]}]},{"field":"90",
"history":[{"history":null,"array":["1"],"values":["Completed
[5]"]}]},{"field":"115","history":[{"history":"03/21/2017","array":["1"],"values":["Final
result[3]"]}]},{"field":"120",
"history":[{"history":null,"array":["1"],"values":["Routine
[6]"]}]},{"field":"205","history":[{"history":null,"array":["1"],"values":["PHARMACY
[420017]"]}]},{"field":"226",
"history":[{"history":null,"array":["1"],"values":["154805044"]}]},{"field":"305","history":
[{"history":null,"array":["1"],"values":["64363[3/21/2017]"]}]},{"field":"310",
"history":[{"history":null,"array":["1"],"values":["35580
[09:53:00]"]}]},{"field":"34030","history":[{"history":null,"array":["1"],"values":
["UNKNOWN, ENTERED BY HISTORY [111111]"]}]},
{"field":"95000","history":[{"history":null,"array":["1"],"values":["5560998855 [3/21/2017
09:54:15]"},{"field":"210>*3*<2060>2061","history":[{"history":null,"array":["2"],
"values":["0060397722"]}]},{"field":"225>4001","history":[{"history":null,"array":["1"],
"values":["ACME HOSPITAL
[4200]"]}]},{"field":"226<8>10110","history":[{"history":"03/21/2017#2",
"array":["1"],"values":["Inpatient
[101]"]}]},{"field":"226<8>18864","history":[{"history":"03/21/2017
2","array":["1","2","3"],"values":["MAIL, LEW [1250]","SMITH, JOHN [215343]", TABLE 6-continued "BROWN, CHARLIE
[987602]"]}]},{"field":"226<8>18875","history":[{"history":"03/21/2017
2","array":["1"],"values":["Emergency [3]"]}]},{"field":"226<8>18882",
"history":[{"history":"03/21/2017#2","array":["1"],"values":["ED02
[373]"]}]},{"field":"226<8>18884","history":[{"history":"03/21/2017
2","array":["1"],"values":["ED02
[2856]"]}]},{"field":"40>.2","history":[{"history":null,"array":["1"],"values":
["CREATININE"]}]},{"field":"40>2000","history":[{"history":"11/21/2016","array":["1"],
"values":["LAB66"]}]}]},{"id":"334836276","name":"","cid":"","status":"Active","fields":
[{"field":".1","history":[{"history":null,"array":["1"],"values":["334836276"]}]},{"field":"30",
"history":[{"history":null,"array":["1"],"values":["Lab
[7]"]}]},{"field":"31","history":[{"history":null,"array":["1"],"values":["5593322522
[3/30/2018
12:42:02]"]}]},{"field":"90","history":[{"history":null,"array":["1"],"values":["Completed
[5]"]}]},{"field":"120","history":[{"history":null,"array":["1"],"values":["STAT
[2]"]}]},{"field":"205","history":[{"history":null,"array":["1"],"values":["EMERGENCY
DEPT
[420008]"]}]},{"field":"226","history":[{"history":null,"array":["1"],"values":
["154806290"]}]},{"field":"34030","history":[{"history":null,"array":["1"],"values":
["RIGGER, BROWN, JAMES
[983817]"]}]},{"field":"34510","history":[{"history":null,"array":["1"],"values":["5593322460
[3/30/2018 12:41:00]"]}]},{"field":"95000","history":[{"history":null,"array":["1"],
"values":["5593897900 [4/6/2018
04:31:40]"]}]},{"field":"210>*3*<2060>2061","history":[{"history":null,"array":["2"],
"values":["0060397944"]}]},{"field":"225>4001",
"history":[{"history":null,"array":["1"],"values":["ACME HOSPITAL
[4200]"]}]},{"field":"226<8>10110","history":[{"history":"04/11/2017
2","array":["1"],"values":["Inpatient[101]"]}]},
{"field":"226<8>18864","history":[{"history":"04/11/2017
2","array":["1","2"],"values":["JOHNSON, RON [987602]","BROWN, BRAD
[57744]"]}]},{"field":"226<8>18875",
"history":[{"history":"04/11/2017 #2","array":["1"],"values":["Emergency
[3]"]}]},{"field":"226<8>18882","history":[{"history":"04/11/2017
2","array":["1"],"values":["ED08[375]"]}]},
{"field":"226<8>18884","history":[{"history":"04/11/2017 #2","array":["1"],"values":["ED08
[2858]"]}]},{"field":"40>.2","history":[{"history":null,"array":["1"],
"values":["ROUTINE UA WITH MICROSCOPIC REFLEX TO
CULTURE"]}]},{"field":"40>2000","history":[{"history":"10/12/2011","array":["1"],"values":
["LAB5822"]}]}]},{"id":"334836277","name":"","cid":"","status":"Active",
"fields":[{"field":".1","history":[{"history":null,"array":["1"],"values":["334836277"]}]},
{"field":"30","history":[{"history":null,"array":["1"],"values":["Lab
[7]"]}]},{"field":"31","history":[{"history":null,"array":["1"],"values":["5593322522
[3/30/2018
12:42:02]"]}]},{"field":"90","history":[{"history":null,"array":["1"],"values":["Completed
[5]"]}]},{"field":"120","history":[{"history":null,"array":["1"],"values":["STAT
[2]"]}]},{"field":"205","history":[{"history":null,"array":["1"],"values":["EMERGENCY
DEPT
[420008]"]}]},{"field":"226","history":[{"history":null,"array":["1"],"values":
["154806290"]}]},{"field":"34030","history":[{"history":null,"array":["1"]...

Typically, handling the different formats of the raw data from different databases is challenging for a vendor application (such as application 134), because application 134 may need to be able to access and process the different formats. In order to address this problem, in some embodiments the raw data is transformed from a way the source system represents it into JSON.

When metaAPI engine 140 receives the raw data response from DQE 144, it may use the response section and formatting rules of the API configuration to transform the response (e.g., into JSON) as set up by the user when developing the API via API configurator 138. Then, metaAPI engine 140 may return the transformed data to application 134. Table 7 provides an example of a record in data transformed from the raw data in Table 6.

TABLE 7

{
"orders":[{
"orderID":"334983051",
    "hospital" : "HOSPITAL [4200]",
    "patientID1" : "0060408296",
    "patientID2" : "154827999",
    "patient_class" : "Emergency [103]",
    "base_patient_class" : "Emergency [103]",
    "current_location_room" : "ED06 [525]",
    "current_location_bed" : "ED06 [5576]",
    "current_location_department" : "ACME Hospital Emergency Department",
    "current_location_facility" : "ACME HOSPITAL [4200]",
    "admission_type" : "Emergency [3]",
    "order_number" : "334983051",
    "order_status" : "Canceled [4]",
    "order_last_update" : "5592607788 [3/22/2018 06:09:48]",
    "ordering_provider_id" : "BRUCE, SCOTT [60236]",
    "ordering_user_location" : "EMERGENCY DEPT [420008]",
    "order_effective_date" : "5592607574 [3/22/2018 06:06:14]",
    "order_type" : "Lab [7]",
    "order_catalog_id" : "LAB293",
    "order_catalog_name" : "CBC WITH PLATELETS DIFFERENTIAL",
    "order_priority" : "STAT [2]",
    "scheduled_time" : "5592607500 [3/22/2018 06:05:00]",
}]
}

In some embodiments, DQE 144 may be a versatile server-side program that performs the following functions in response to requests, including: executing a query based at least in part on constraints that then yields a result set, where the result set includes one or more database records corresponding to the query; for a given record in the results set, DQE 144 may retrieve the requested fields in database 136; and/or the results and corresponding data are then bundled by DQE 144 into a response that, depending on the architecture involved (e.g., a cloud-based service including a JSON payload that uses a hypertext transfer protocol or HTTP, a condensed string of data that uses a JAVA connector with TCP/IP, or the information may be presented on a display in a debug mode), may be returned to metaAPI engine 140. Note that DQE 144 may retrieve its information and data from, e.g., an EHR cache server for database 136 (such as an HER database from Cerner Corporation). Consequently, DQE 144 may be written in coding language that is native to database 136. Moreover, DQE 144 may be design so that a single routine or file of code may be capable of searching and creating a result set of records across database 136. Furthermore, DQE 144 may be agnostic to the master files or tables that are accessed, the fields involved, the operators executed against those fields, and/or the values used in comparisons.

Additionally, operation of DQE 144 may be understood in terms of three systems: a system in which a request that is generated by a third-party application (e.g., an end-user focused user-interface application, a server-side batch process, etc.) is sent to metaAPI engine 140; an intermediary system that executes code for metaAPI engine 140 (such as Java code); and a database 136 that includes DQE routines 152. Note that the requester (application 134) may not communicate directly with DQE 144. Instead, metaAPI engine 140 may mediate communications. As discussed previously, there may be a preliminary operation that creates a given API based at least in part on an API configuration. After deployment, this API configuration may be moved to a landing zone or database (such as flexDB 146) where metaAPI engine 140 may recognize its presence, consume the content of the API configuration, and then dynamically generate the API. Note that a third-party requestor (such as application 134) may: run a specific API, execute a query by calling a metaAPI engine endpoint on API computer 124, and may specify a particular API configuration identifier with stored configuration information that is used to create a DQE call.

For example, consider an API call (e.g., config ID #13) that is designed to generate a list of surgical departments, where the parameter of interest is a service area. Assume, e.g., that there are five service areas, and a given service area may have multiple locations/surgical departments. Stated differently, the API may be configured to access data on surgical departments and may need a single parameter, the 'service area ID.' In this process, application 134 may send metaAPI engine 140 a request to execute config ID #13 using, e.g., service area 4 as a constraint. In response, metaAPI engine 140 may access the API configuration for config ID #13, and may use the information in this API configuration to construct a well-formatted request to DQE 144, including a constraint that is specific to the service area. Then, metaAPI engine 140 may send the appropriately formatted request to DQE 144 via, e.g., a JSON payload, an interconnect, or a Java connector. Note that the metaAPI request may have a standard format, and may include: one or more constraints, an initial master file, a list of items and data fields that will be retrieved, and/or a flag that instructs DQE 144 which pathway to use for sending information (e.g., an interconnect, Java, etc.). When DQE 144 receives the request, it may execute the query, access the relevant department information. The information at this point may be in a technical database-standardized format. MetaAPI engine 140 may translate the technically formatted content into another format that is machine consumable and readable (such as JSON), as specified in the API configuration. Then, application 134 may receive formatted, condensed and readable information, such as a list of the surgical departments that are in service area 4.

In summary, the disclosed embodiments may be implemented using interacting components: DSE 142 that retrieves database metadata in source code 154 and determines metadata changes, and API configurator 138, DQE 144 and/or metaAPI engine 140 that perform real-world transactions using real-time data provided by DQE 144. In contrast with existing approaches, in which an API has a structured format that persists, a given API configuration persists and is a proxy for a given APU, which is built on the fly in response to a user call from application 134.

Moreover, in existing approaches that use APIs, there may be a server with an endpoint that is called to obtain, e.g., patient data. When this endpoint is invoked and patient identifier (such as a medical record number) is passed, the server may call a code routine on the server specifically designed to get specific patient data, and this routine may pull the patient data and return it to the server, which, in turn, returns the data to the requester. In contrast, in the disclosed techniques, there may be a single endpoint on API computer 124, the metaAPI endpoint. This single endpoint may be used to perform multiple operations (e.g., for an arbitrary number of APIs specified by an arbitrary number of API configurations). When the metaAPI endpoint is invoked and identifier(s) of one or more API configurations to execute are provided, metaAPI engine 140 may perform the remaining processing, including: interpreting the contents of the API configuration, determining what needs to be sent to DQE 144 and when, and then may call DQE 144.

As discussed previously, after application 134 is in production, it may be prone to malfunctioning because of unexpected changes, variation, or gaps in one or more source data elements that are used by application 134. These problems may be the result of unexpected variations in data, unexpected changes to a source data field location (e.g., structural changes), unexpected changes to source data field attributes and/or variation in the returned data for requested fields (e.g., content changes). Note that data-field attributes may be defined as the metadata about the field. For example, for a field called 'order type,' the field attributes may include that it: is a text field, has eight characters, has a label, has help text, and/or is related to another field in another file.

Structural changes may include actual changes to the location of a data field, which may be made by a vendor. These types of changes are often the easiest to detect, but typically the least common (approximately 5%). For example, an EHR vendor may decide to consolidate multiple blood pressure data fields and to reassign them to a single, new field in the source system database. However, a B2B (such as a HIT vendor) may not be told about the new field and, thus, may continue to call blood pressure values from the old data fields. When no data are returned for a call to a patient record, the initial assumption may be that blood pressure was not collected from the patient during the encounter. Moreover, initially it may not be possible to distinguish between data not being collected versus data this is no longer captured in the defined field. Ultimately, an end user or HPG staff may report that there has been a sudden drop off in the use of the application. End users may also just stop accessing the application, but may not notify the information-technology staff or the B2B. Eventually, the B2B staff charged with monitoring the application may notice the anomaly (i.e., that they are accessing other encounter data, but not data on blood pressure) and then may decide to investigate.

Moreover, there are types of data content issues that occur, either because of an explicit change or because the data attributes in a defined field differ from what is expected. Each of the content factors may cause an application to malfunction or fail because of the difference between the data that an application receives versus the data that the application expected. Content change or variation are often the dominant type of data problem (approximately 90%) and usually are the least likely to be documented.

Furthermore, there may be unexpected changes to the data location. Notably, from time to time, EHR staff or other EHR users may change the location where a data element is stored. This differs from a structural change, in which a current field is moved to another location. In the case of unexpected changes to the data location, the data fields may not be physically moved, but the EHR staff may have relocated the data to a different, preexisting field. For example, an HPG neurology service may decide on a new administrative procedure and may instruct staff to enter a caregiver name in the 'social determinants' field instead of the 'other information' field. This type of administrative change is typically idiosyncratic and is almost never documented or disseminated to other users of the data fields. When the application accesses the social determinants field it may be expecting data on social determinants with specific attributes, not information on caregivers. If the application is looking for caregiver information in a caregiver field, it may find a null value. The default assumption may be that the patient does not have a documented caregiver, versus the reality that the data on caregiver may be in a different field. Eventually, this error may be detected, because an end user of the application or other HPG staff may report it, or because one of the B2B staff charged with monitoring the application notices a drop in the number in patients for whom a caregiver is recorded and may decide to investigate.

Additionally, there may be unexpected changes to data attributes. Notably, data field attributes (e.g., metadata about the field itself) may be modified without notification. For example, a B2B may be using a 'laboratory test results' field that has the field attributes including: text; up to 8 characters, a label, help text, and/or is related to another field in another file. The HPG may decide to change the laboratory test result 'text' attribute to 'integer' in order to convert historical text values into a more useable form for plotting results, and then may continue using the integer format going forward. This change may be poorly documented and even more poorly disseminated to those who use this data field. Consequently, B2Bs using this field may not be prepared to receive an integer in the field and their applications may malfunction.

In some embodiments, there may be unexpected variation in return data. Notably, unexpected variation in the returned data may occur for reasons that are not explained by a prior actual change to field-level data attributes. B2Bs and other users may not understand that the data that actually appear in a given field may have attributes that differ from the field attributes documented in metadata. For example, a B2B may be using a field called 'laboratory test results' to retrieve data for a kidney function (e.g., eGFR) laboratory test that they use in a predictive technique (such as a classifier or a regression model). Attributes for this field may describe a range of acceptable values (e.g., 10-110), but the field may also include values outside of this range without it being an error. When the application from this B2B is in production, it may experience the volume and variation of real-world data for eGFR compared to the more limited variation experienced in the test environment. Moreover, when out of range values occur, the predictive technique may be unable to accommodate the values that are out of range and may malfunction (e.g., the application may not be able to run the predictive technique, an error may occur, and an incorrect result may be generated).

While changes and variation are common in healthcare, they are largely undocumented and often occur with little or no notification to users of the data. It is often the HPG end user (e.g., physicians, nurses, etc.) or their information-technology staff who notify the B2B that their application is not working. Moreover, data changes and variation are a common reason for application malfunctions. However, when the B2B is notified of the malfunction, they usually do not know if it is because of data changes and variation or another reason. Even if they do know the type of malfunction, they usually do not know the cause. This is because the HPG typically does not know the cause of the error at the time they report it to the B2B. Furthermore, the default position of the HPG is usually that they are not responsible for application malfunction and that the problem belongs to the B2B. Consequently, the B2B may have to identify the cause and then fix the problem with very limited support from the HPG. Additionally, the B2B typically may need to repeat the operations in the path-to-production process to reinstall the application. With time, the B2B may have to increase client-management staffing, moving away from their vision to be a software-as-a-service or a software-component company into a consultancy or a service company with software. This business process may occur along with other threats, including loss of confidence in the application by the HPG users.

In some embodiments of the disclosed techniques, API computer 124 may include a dynamic data change module (DCM) 156 that detects and addresses data changes and variation. Notably, DCM 156 may perform functions including: automatically detecting data changes and variation in relation to expectations of the application that provides a user call; and performs a remedial action, such as alerting the B2B or HPG before there is an impact on the users and/or makes a recommendation for how to address the problem. Thus, DCM 156 may automatically send a notice that the data called by an API has changed and may recommend that the configuration file be updated.

DCM 156 may reduce or eliminate risks, including: an application malfunction; the need to take the application out of production to fix it; 3) the need to spend time and resources to identify the cause of the malfunction; the need to spend time and resources to fix the application; and/or the need to repeat the operations in the path to production in order to apply the code fix.

In the disclosed techniques, DCM 156 may detect data change and/or variation using DSE 142, a checksum, a schema-level string that describes a data field in detail, and/or one or more user-defined rules for a given field to determine whether there has been a data structure, content and/or context (such as a workflow) change to a given data field used by a specific application. Note that the one or more user-defined rules may set expectations for what is considered acceptable data for a specific field. These rules are created by using API configurator 138. However, the one or more user-defined rules may not be needed to detect structural changes, because DSE 142 may provide a map for what fields are available and where they are located.

The one or more user-defined rules and/or DSE 142 may be referenced by or incorporated into a checksum to detect changes. Notably, a checksum may be used to determine if the metadata for a data field has changed (such as a label of the field, a type of the field, if the field has been added to an index, etc.). Moreover, a checksum may be used to determine if the content and/or context of the data from a data field in response to a data query varies from an expected set of values for a field. For example, an entry of 'male' or 'female' may be expected for a 'gender' field. If, e.g., the checksum for the gender field with 'male' or 'female' may be '30284.' Then, when the value in the gender field for a record comes is 'unknown,' the checksum may no longer be '30284.' In some embodiments, DCM 156 may use a filter to compare returned data to expectations.

Similarly, in some embodiments, a schema change checker may detect field-level structural change. Notably, the schema change checker may use DSE 142 and a checksum to detect physical changes made to the source system metadata at the field level.

Moreover, a content change checker may detect a field-level content change. Notably, the content change checker may use DSE 142, a checksum, and/or one or more user-defined rules to detect unexpected changes to data location, unexpected changes to data attributes, and/or unexpected variation in return data.

Note that in order to assist with unexpected variation in return data, DCM 156 may run analytics for data quality and completeness based at least in part on content rules. For example, if a B2B provides a rule that indicates a liver function laboratory test may have an integer value between 1-45, DCM 156 may run analytics in order to determine how often there are values outside of the 1-45 range, do they ever include text, etc.

In some embodiments, one or more user-defined rules for content changes may include: a schema rule (e.g., a value type may only be valid if it includes a laboratory test or a radiology order); an expected value rule (e.g., a rule for unexpected changes to data location may be that a field may not be empty, a rule for unexpected changes to data attributes may be that a field has an integer value, etc.); an error exception rule (e.g., handling content changes, such as when there is a different value that an expected value or when expected data is not received, by providing a warning message).

Moreover, a change may be detected at a batch level or based at least in part on a predefined schedule (e.g., daily). For structural changes, DCM 156 may perform real-time schema checking at the EHR extractor level. Moreover, for content changes, DCM 156 may detect changes in real time. While the capabilities of DCM 156 may be used in conjunction with data streams associated with dynamic APIs, in other embodiments DCM 156 may be used with other healthcare data streams (such as HL7) and/or non-healthcare data.

When a change is detected, DCM 156 may perform a remedial action. Notably, the remedial action may include providing a notification with details of a data element that is the problem. Alternatively or additionally, the remedial action may include an update to an API configuration (such as changing a transformation) and reissuing a codeless API.

For example, DCM 156 may notify a B2B that there has been a change, and may optionally provide information on the nature of the change and one or more recommendations on what to do about the change (e.g., what field to use if the field location changed, even if the change is not caused by the vendor). Notably, if a null value was received and this was at odds with one or more expected value(s), it may indicate that the field is no longer being used or was moved. In response, a schema check may be performed to see if a new field is identified.

Note that a recommendation may be inherent to the information that was provided. For example, detection of a content form (e.g., 'unknown' for gender) or a format (e.g., 'text' instead of 'integer') that is different from what is expected may mean that this is an unexpected variation if there was no corresponding change that was detected to the metadata. In this example, the B2B or owner of an application may be able to assess whether to update the expected format using API configurator 138. More generally, after the B2B or owner of an application is alerted about a change, they may use API configurator 138 to modify their API configuration(s) in order to account for the change(s) or variation(s). In some embodiments, DCM 156 may offer a self-repair (e.g., default values) option for a user to accept and approve, so that one or more API configurations maybe automatically updated by API configurator 138.

Moreover, if a new field was created to replace an existing field, an update may be semi-automated by presenting information to the user, such as: an unexpected null value that was detected for the old field along with one or more newly identified fields in a review of the dynamic schema from DSE 142. Then, the user may choose a newly identified field to replace the existing field, and the corresponding API configuration may be accordingly updated by API configurator 138. Alternatively or additionally, if a new field name was provided for the same concept, then API configurator 138 may add a mapping to the corresponding API configuration.

In some embodiments, DCM 156 may provide an alert or a notification based at least in part on a context or workflow. For example, when an expected action is not taken (and data do not show up in an expected field), an alert may be provided to an HPG end user (such as a physician in an emergency department), so that they can take preventive or corrective action.

Furthermore, DCM 156 may perform a preventive or corrective based at least in part on change in a process or workflow synchronicity, or gaps in what should exist, be performed, and/or be documented that can result in an error (which collectively are sometimes referred to as 'context'). Notably, DCM 156 may use a set of rules (such as relationships between data elements, which may be user defined, predefined and/or dynamically learned) for a type of 'transaction' and that may involve an associated workflow. For example, a patient may be admitted to the emergency department and may have a high-risk of readmission. This may be a type of a transaction. In this example, a 'primary care provider' (PCP) field may be filled in or there may be an PCP appointment scheduled post-discharge. Consequently, 'context' may involve monitoring a process or workflow. If something in this process or workflow is incorrect or is not working, DCM 156 may provide an alert, e.g., a page, a text, an email, a notification in a user interface, etc.

In some embodiments, a data context may refer to a network of connections or relationships among two or more data fields that are created as metadata, where the network of data yields or is associated with information. Alternatively or additionally, a data context may be identified and represented in a different form (e.g., a difference, a ratio) for specific use cases. Note that contextual metadata may add value, by making it possible to extract additional information from data, as opposed to a single datum for which the information is typically restricted to its value.

Moreover, a context-related gap may be the result of changes in the expected micro (data) workflows, including missing operations. Detecting context gaps may be useful when there are workflows that involve multiple people, systems, and/or organizations. Context gaps may be valuable, because this is where things fall through the cracks and workflows break down. Thus, context gaps may add cost, can impact quality and/or may lead to bad patient outcomes and/or experiences.

Furthermore, 'context' may be defined using rules set up by a B2B for their application. For example, a B2B may have an application that assesses a risk when a patient is admitted to the emergency department. If the patient is at high risk, the application may provide a message that a social worker should be assigned (if this has not already occurred). The application may use emergency-department transaction data (for emergency-department admissions), clinical and social determinant data (e.g., to assess risk), and/or order data (e.g., for social worker assignment). However, the application may only receive an emergency-department transaction and clinical and social determinant data, but may not receive order data, even through a nurse made the order for the social worker because of a queuing problem in a user-interface engine. The application may be unaware there is a queuing problem and, thus, may present a message that indicates a social worker needs to be assigned. This error may cause a number of problems. Notably, another member of the care team may need to take time to repeat the order, thereby causing a duplicate order and wasting time of the care team, which may cause the care team to distrust the application.

In another example, when DCM 156 detects an emergency-department admission, it may expect other things (outside of the emergency-department transaction) to occur and, if not, it may provide an alert. For example, an HPG may have specified or set the rules, such as, when there is an emergency-department admission, the patient may be expected to have a case order for a care management system. Thus, when an emergency-department admission detected, but not the case order, DCM 156 may provide an alert. Alternatively, when there is a high-risk emergency-department admission, but a social worker is not assigned, DCM 156 may provide an alert.

Moreover, one or more user-defined rules may be used to detect a blank data field in relation to one or more other fields. When a blank data field is detected, DCM 156 may provide a soft message (such as a warning) to a user of an application and/or by sending an alert to the B2B that provides the application.

In some embodiments, DCM 156 may use a machine-learning technique (such as a pretrained classifier or a regression model, which may be trained using a supervised-learning technique) and/or a pretrained neural network (such as a convolutional neural network, a recursive neural network, etc.) to analyze data to identify workflows, determine a potential problem or error in a given workflow, and/or to selectively perform a remedial action when a potential problem or error is found.

In some embodiments, the potential problem or error in a given workflow may include: a wrong item or field used, over-mapping, label renaming and/or an incorrect mapping. For example, if an HPG staff member wants a patient identifier, an information-technology group may interpret what the HPG staff member wants. Notably, they may take a patient medical record number that is used 95% of the time and transform it into a patient identifier in database 136. However, subsequently the HPG staff member may notice that there are missing laboratory test orders. After two days of research, the HPG staff member may determine that they are not missing any laboratory orders. Instead, they do not have the correct patient identifier.

Moreover, if an HPG staff member wants to include an emergency department in an application, so the HPG staff member may ask the information-technology group for emergency-department identifiers to be added to the application. The information-technology group may determine that there are four emergency departments, each with their own identifier, location and name. However, the information-technology group may update the application to include a generic 'emergency department.' Consequently, when the HPG staff member tries to figure out workflows based at least in part on location, they may be unable to do so because the information-technology group transformed the four emergency departments into one. Therefore, the HPG staff member may need to have the information-technology group enter discrete information for the four emergency departments, which may result in repeating the operations in the path to production and, thus, months of delay.

Furthermore, an HPG staff member may ask for a 'study code,' which is actually a Current Procedural Terminology (CPT) code. This is a transformation of a 'label,' not of content. Consequently, when there is a new CPT code to be added and the HPG staff member provides a request, the information-technology group may not know what they are referring to.

Additionally, if an HPG staff member wants a list of the providers in the emergency department, they may ask the information-technology group the list. Database 136 may include a 'provider type' field, and the information-technology group may put the provider list into this field. However, the information-technology group may use this field for multiple different types of providers, such as physicians, doctors of osteopathic medicine, physician assistants, etc. The HPG staff member may not know this. They may assume that the provider type field is only for physicians.

In these ways, API computer 124 and computer 126 may allow data in database 136 to be efficiently, flexibly and robustly accessed in real time. These capabilities may allow this data to be used in a wide variety of applications, thereby allowing the asset value of the data to be leveraged, e.g., by HPGs, payors, HIT vendors and patients. In the context of EHRs, the disclosed schema techniques, the generating techniques, the query techniques and the monitoring techniques may allow long-standing problem of data integration and interoperability to be addressed, which may enable applications that offer improved outcomes and reduced costs. For example, applications and reports may be implemented in significantly less time (weeks versus months), with commensurate reductions in effort, complexity and cost. In the process, the disclosed techniques may eliminate break-fix cycles and may allow applications to be routinely and reliably updated. Collectively, these capabilities may enable communication between different entities (e.g., provider to payer, provider to provider, etc.) and within an entity, and may reduce infrastructure and development and management overhead.

Figure 2:
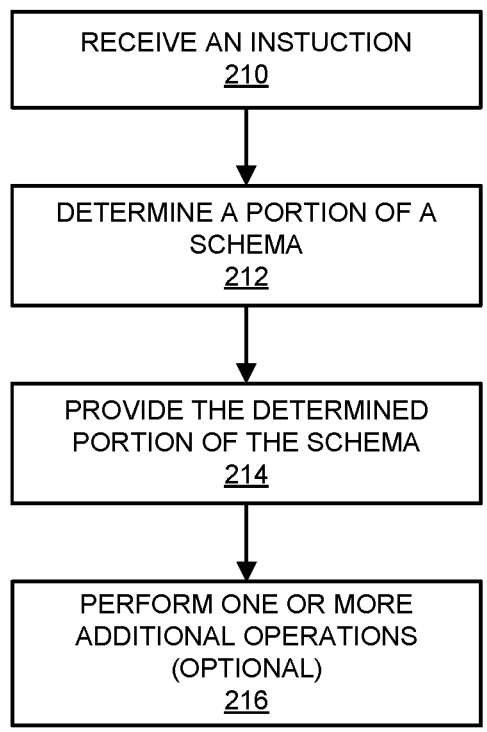
FIG. 2 is a flow diagram illustrating an example of a method for determining a dynamic schema for a database using a computer of FIG. 1 in accordance with an embodiment of the present disclosure.

We now describe embodiments of a method. FIG. 2 presents a flow diagram illustrating an example of a method 200 for dynamically determining a portion of a schema, which may be performed using a computer (such as computer 126 in FIG. 1).

During operation, the computer may receive an instruction (operation 210) to dynamically determine the portion of a schema of a database, where the instruction specifies a field in the database and the portion of the schema is initially unknown or unavailable to the computer. Note that the instruction may: be associated with a predefined schedule; be in response to an upgrade to the database; be in response to an error in an application that uses data associated with the field; be in response to an error in an API associated with the application; or occur when the API associated with the application is called.

Then, the computer may determine the portion of the schema (operation 212) based at least in part on the instruction, where the determining includes interacting, via a network interface with a second computer and interpreting source code associated with the database, and the portion of the schema includes information specifying the field and contents associated with the field.

Note that the information may specify an interrelationship between the field and a second field in the database. Additionally, the information specifying the field may include a name of the field. Moreover, the information may include a type of data. For example, the type of data may include an order type, such as: a medication order, a laboratory test, and/or a procedure order. In some embodiments, the information may include a format of the field.

Moreover, the computer and the second computer are at different locations and/or may be associated with different organizations or entities. Furthermore, the database may be associated with EHR software and may include patient medical data.

Additionally, the contents may include a value associated with the field.

Next, the computer may provide the determined portion of the schema (operation 214).

In some embodiments, the computer may optionally perform one or more additional operations (operation 216). For example, the computer may not store the portion of the schema after the portion of the schema is determined.

Moreover, the computer may receive a second instruction to dynamically determine a second portion of a schema of the database, where the instruction specifies a second field in the database and the second portion of the schema is initially unknown or unavailable to the computer. Then, the computer may determine the second portion of the schema based at least in part on the second instruction, where the determining comprises interacting, via the network interface with the second computer and interpreting the source code, and the second portion of the schema may include second information specifying the second field and contents associated with the second field. Next, the computer may provide the determined second portion of the schema.

Figure 3:
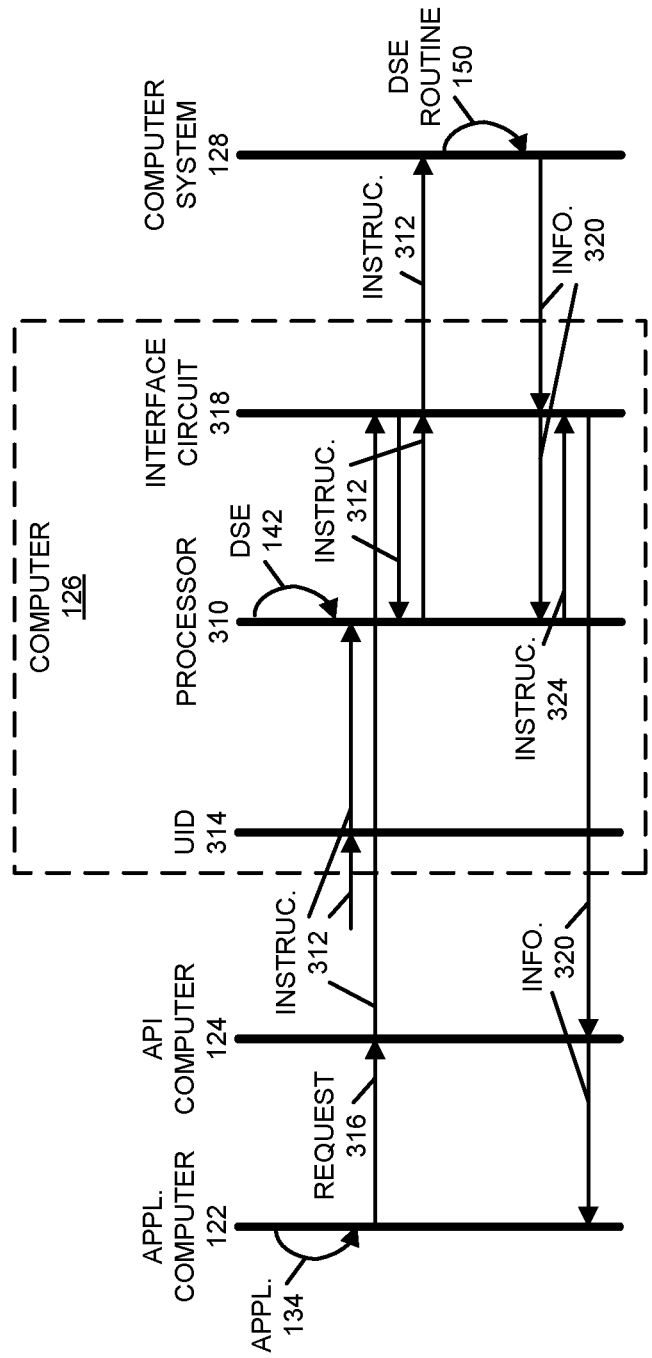
FIG. 3 is a drawing illustrating an example of communication among electronic devices in FIG. 1 in accordance with an embodiment of the present disclosure.

FIG. 3 presents a drawing illustrating an example of communication between application computer 122, API computer 124, computer 126 and computer system 128. Notably, a processor 310 in computer 126 may execute DSE 142. Moreover, a user may provide an instruction 312 to dynamically determine a portion of a schema of database 136. This instruction may be received by user-interface device (UID) 314 in computer 126, such as: a keyboard, a mouse, a touchscreen, a trackpad, a voice-recognition interface, etc. Then, user-interface device 314 may provide instruction 312 to processor 310.

Alternatively, an application (such as application 134) executing on application computer 122 may provide a request 316 for the data to API computer 124. Then, program instructions executed on API computer 124 (such as program instructions for a dynamic API, which may be executed by metaAPI engine 140) may provide instruction 312 (which are based at least in part on request 316) to computer 126. Next, an interface circuit 318 in computer 126 may receive instruction 312 and may provide instruction 312 to processor 310.

Based at least in part on program instructions associated with DSE 142 and instruction 312, processor 310 may determine the portion of the schema. For example, processor 310 may provide instruction 312 to interface circuit 318, which then provides instruction 312 to computer system 128.

After receiving instruction 312, program instructions executed on computer system 128 may determine the portion of the schema. For example, DSE routine 150 may read source code 154 associated with database 136 to determine the portion of the schema. Then, computer system 128 may provide information 320 that specifies the determined portion of the schema to computer 126.

Moreover, after receiving information 320, interface circuit 318 may provide information 320 to processor 310. Based at least in part on program instructions associated with DSE 142 and information 320, processor 310 may provide 322 the determined portion of the schema. For example, processor 310 may display the determined portion of the schema. Alternatively, processor 310 may instruct 324 interface circuit 318 to provide information 320 to API computer 124. In response, API computer 124 may provide information 320 to application computer 122 and, thus, to application 134. Note that the determined portion of the schema may not be stored in memory in computer 126.

Figure 4:
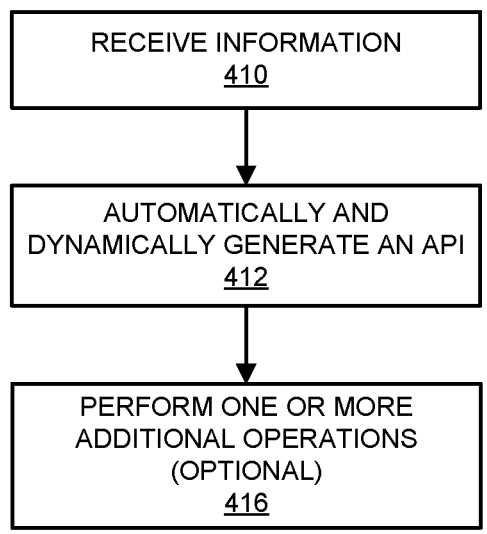
FIG. 4 is a flow diagram illustrating an example of a method for dynamically generating an API using a computer of FIG. 1 in accordance with an embodiment of the present disclosure.

FIG. 4 presents a flow diagram illustrating an example of a method 400 for dynamically generating an API, which may be performed by a computer (such as API computer 124 in FIG. 1). During operation, the computer may receive information (operation 410) that specifies an API configuration, where the API configuration includes second information specifying data associated with a database (which may be accessed via a data-query engine that is implemented by a second computer), and desired results of a query for the data that are used by an application (which may be implemented by a third computer).

Note that the second information may include: third information specifying one or more fields in the database, constraints of the data, and/or a dynamic constraint that specifies one or more instances of the data in the database. For example, the constraints on the data may include: a type of the data, a format of the data, a range of values of the data, a patient identifier, a department identifier, an identifier of an organization, and/or an operational constraint. Moreover, the operational constraint may include: an inequality operation, an equality operation, an inclusion operation, an exclusion operation, a starting symbol, an end symbol, and/or a length operation. Furthermore, the constraints on the data may include: whether an ordered medication was picked up, whether an ordered procedure was performed, and/or or whether an ordered medical test was performed. Additionally, the third information may specify different fields in the database.

Furthermore, receiving the information may include accessing the API configuration in the memory and/or receiving user-interface activity that specifies the API configuration. Additionally, the API configuration may correspond to natural language that is received by the computer.

In some embodiments, the API may be associated with an endpoint or address in the computer that is common to multiple APIs.

Note that the API may include abstraction layers and configuration settings instead of the predefined or preprogramed software.

Moreover, the second computer and/or the third computer may be different from the computer.

Then, the computer may automatically and dynamically generate the API (operation 412) based at least in part on the API configuration, where the API is not specified using predefined or preprogramed software.

In some embodiments, the computer may optionally perform one or more additional operations (operation 414). For example, the API may: provide, to the second computer, an instruction for the query for the data based at least in part on the second information; receive results of the query associated with the second computer, where the results comprise raw data; transform the raw data into the data based at least in part on the desired results; and provide the data. For example, the transformation may convert the raw data into a readable format for the third computer. Moreover, the computer may provide the data addressed to the third computer.

Furthermore, the computer may receive a request for the data associated with an application, and the API may be automatically and dynamically generated in response to the request.

Figure 5:
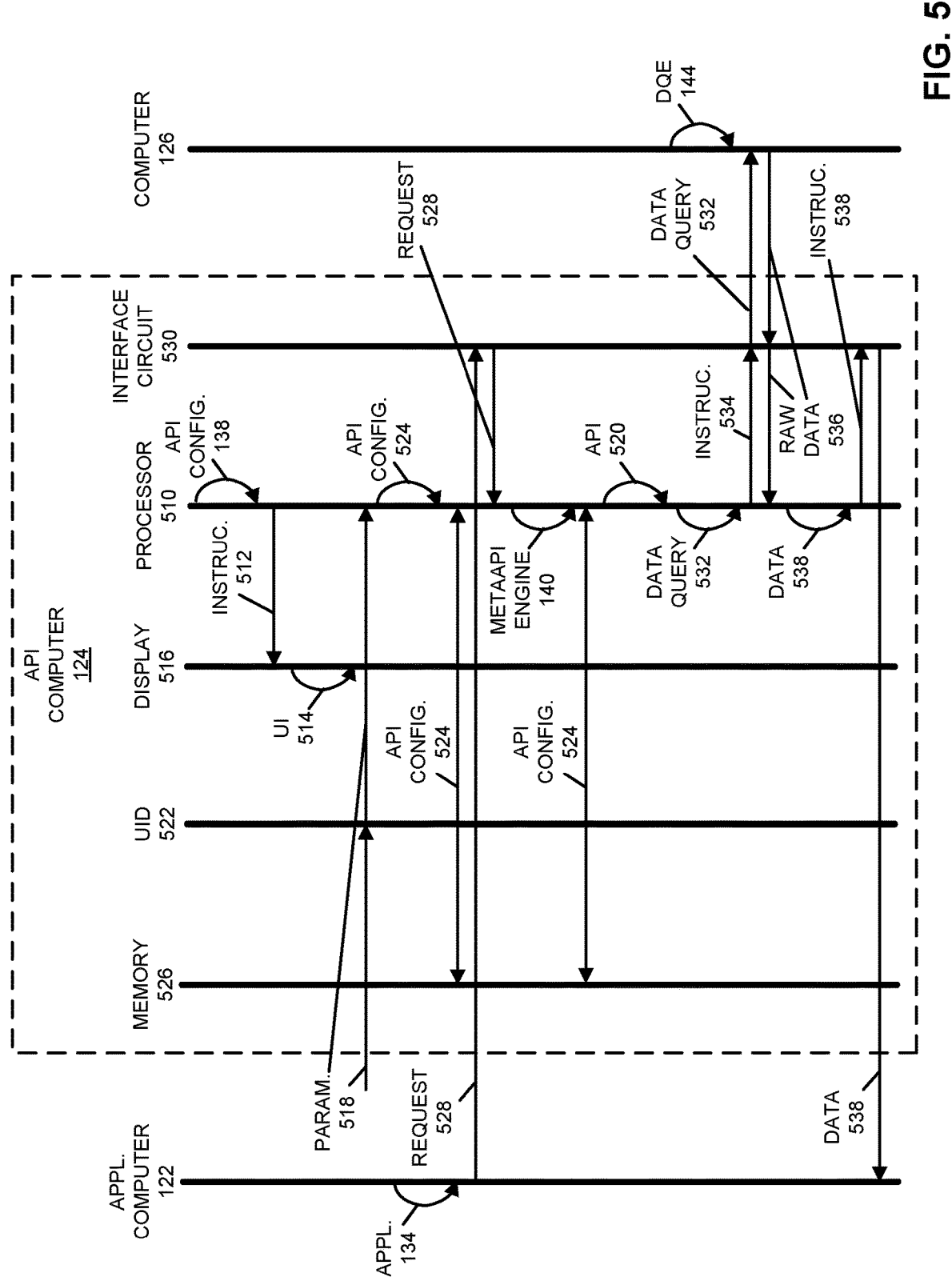
FIG. 5 is a drawing illustrating an example of communication among electronic devices in FIG. 1 in accordance with an embodiment of the present disclosure.

FIG. 5 presents a drawing illustrating an example of communication among application computer 122, API computer 124, computer 126. Notably, a processor 510 in API computer 124 may execute API configurator 138. Based at least in part on program instructions associated with API configurator 138, processor 510 may provide instructions 512 for a user interface (UI) 514 to display 516 in API computer 124, which displays user interface 514.

Moreover, a user may use user interface 514 to provide selections of parameters 518 for an API 520 to user-interface device (UID) 522 in API computer 124, such as: a keyboard, a mouse, a touchscreen, a trackpad, a voice-recognition interface, etc. Then, user-interface device 522 may provide parameters 518 to processor 510. Based at least in part on the selected parameters 518, program instructions associated with API configurator 138 may generate or create API configuration 524, which is stored in memory 526 in API computer 124.

Next, an application (such as application 134) executing on application computer 122 may provide a request 528 for data 538. After receiving request 528, an interface circuit 530 in API computer 124 may provide request 528 to processor 510. In response, processor 510 may execute metaAPI engine 140. Based at least in part on program instructions associated with metaAPI engine 140 and API configuration 524 (which may be access in memory 526), processor 510 may dynamically generate API 520.

API 520 may determine a data query 532 based at least in part on request 528 and API configuration 524. Then, processor 510 may instruct 534 interface circuit 530 to provide data query 532 to computer 126. As described further below with reference to FIGS. 6-7, DQE 144 executed by computer 126 may interact with computer system 128 to obtain raw data 536, which is provided to API computer 124.

After receiving raw data 536, interface circuit 530 may provide raw data 536. Based at least in part on program instructions associated with metaAPI engine 140, API configuration 524 and raw data 536, processor 510 may transform raw data 536 into data 538. Then, processor 510 may instruct 540 interface circuit 530 to provide data 538 to application computer 122 and, thus, the application.

Figure 6:
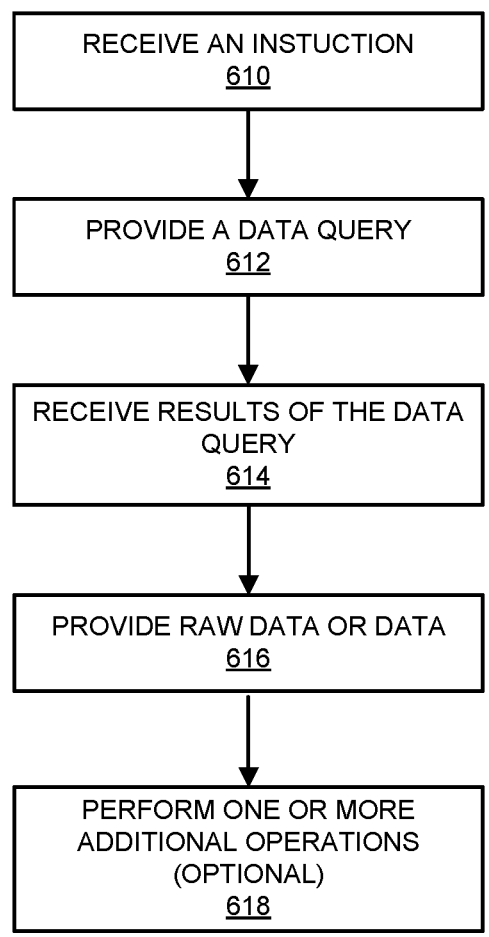
FIG. 6 is a flow diagram illustrating an example of a method for providing raw data or data using a computer of FIG. 1 in accordance with an embodiment of the present disclosure.

FIG. 6 presents a flow diagram illustrating an example of a method 600 for providing raw data or data, which may be performed by a computer (such as computer 126 in FIG. 1).

During operation, the computer may receive, from a second computer (which may implement an API), an instruction (operation 610), where the instruction includes information specifying the data associated with a database and a dynamic constraint that specifies one or more instances of the data in the database.

Note that the dynamic constraint may include: a patient identifier, a department identifier and/or an identifier of an organization.

Moreover, the database may be associated with EHR software and may include patient medical data.

Then, the computer may provide a data query (operation 612) to the third computer that implements the database, where the data query is based at least in part on the instruction.

Note that the data query may specify one or more locations in the database. Moreover, the data query may be based at least in part on a dynamic schema of a portion of the database. The portion of the schema of the database may not be stored in the computer.

Furthermore, the computer, the second computer and the third computer may be at different locations.

Additionally, the computer and the third computer may be associated with different organizations or entities. Alternatively, the computer and the second computer may be associated with a common organization or entity.

Moreover, the computer may receive results of the data query (operation 614), where the results include the raw data corresponding to the data.

Next, the computer may provide the raw data or the data (operation 616) addressed to the second computer.

In some embodiments, the computer may optionally perform one or more additional operations (operation 618). For example, the computer may: provide, to a fourth computer (which may or may not be different from the computer), a request for the dynamic schema of the portion of the database based at least in part on the information; and receive, from the fourth computer, the dynamic schema of the portion of the database.

Figure 7:
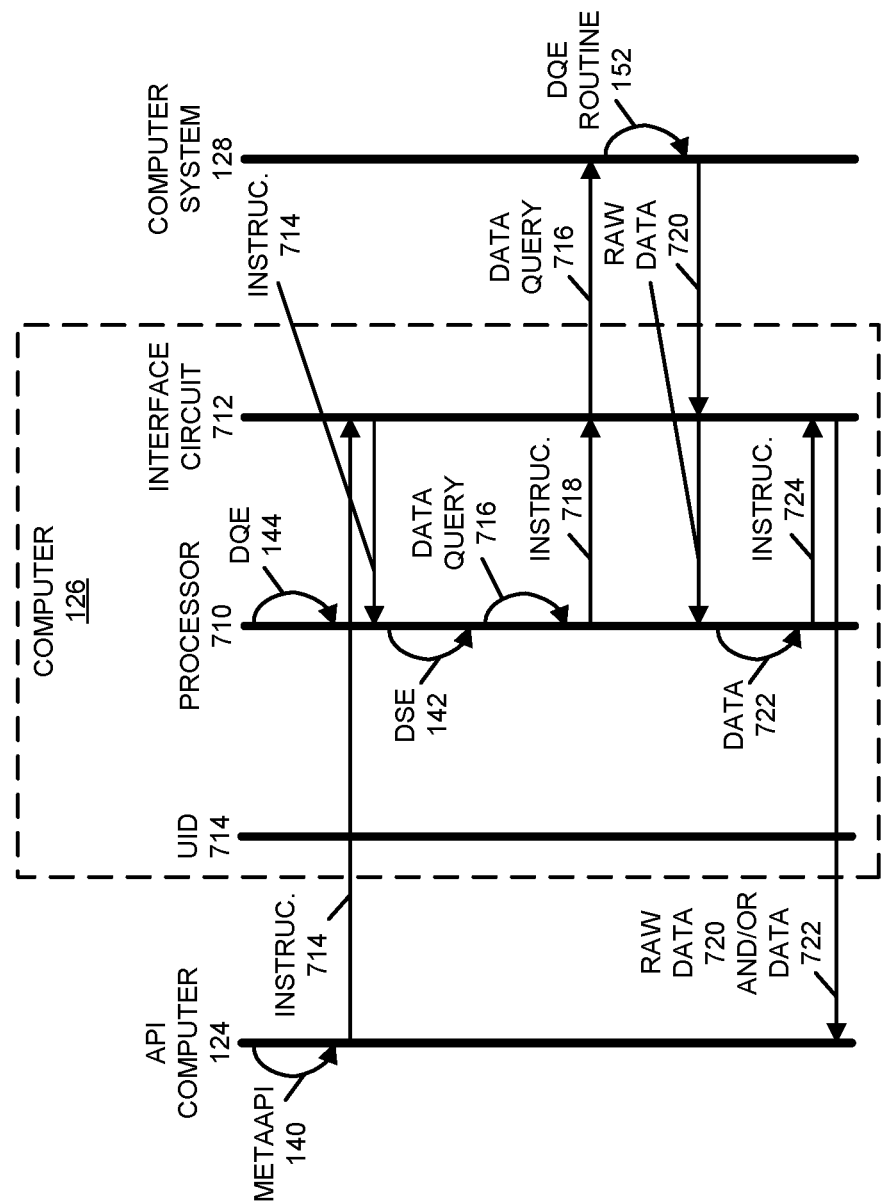
FIG. 7 is a drawing illustrating an example of communication among electronic devices in FIG. 1 in accordance with an embodiment of the present disclosure.

FIG. 7 presents a drawing illustrating an example of communication among API computer 124, computer 126 and computer system 128. Notably, a processor 710 in computer 126 may execute DQE 144. Moreover, an interface circuit 712 in computer 126 may receive an instruction 714 from a dynamic API generated by metaAPI 140 on API computer 124 (as described previously with reference to FIGS. 4-5), which may provide instruction 714 to processor 710.

Based at least in part on program instructions associated with DQE 144 and instruction 714, processor 710 may create or generate a data query 716 for data 720. Note that creating or generating data query 716 may involve interaction with DSE 142 that is executed by processor 710, and which may dynamically provide at least a portion of a schema associated with database 136 (as discussed previously with reference to FIGS. 2-3). Then, processor 710 may provide an instruction 718 to interface circuit 712. In response, interface circuit 712 may provide data query 716 to computer system 128.

After receiving data query 716, program instructions executed on computer system 128 may obtain raw data 720 from database 136. For example, DQE routine 152 may obtain raw data 720 from database 136. Then, computer system 128 may provide raw data 720 to computer 126.

Moreover, after receiving raw data 720, interface circuit 712 may provide raw data 720 to processor 710. Based at least in part on program instructions associated with DQE 144 and raw data 720, processor 710 may optionally transform raw data 720 into data 722. Then, processor 710 may provide an instruction 724 to interface circuit 712. In response, interface circuit 712 may provide raw data 720 and/or data 722 to API computer 124.

Figure 8:
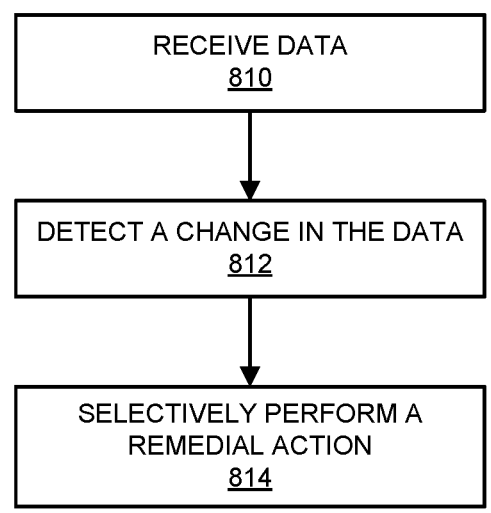
FIG. 8 is a flow diagram illustrating an example of a method for detecting a change and selectively performing a remedial action using a computer of FIG. 1 in accordance with an embodiment of the present disclosure.

FIG. 8 presents a flow diagram illustrating an example of a method 800 for detecting a change and selectively performing a remedial action, which may be performed by a computer (such as API computer 124 in FIG. 1).

During operation, the computer may receive data (operation 810) associated with a second computer and a database, where the second computer implements a data-query engine for the database.

Note that the second computer may be different from the computer. Moreover, the database may be associated with EHR software, and the database and the data may include patient medical data.

Then, the computer may detect the change in the data (operation 812) based at least in part on one or more of: a schedule of when to check for the change; a location in the database associated with the data; expected content of the data; an expected context of the data; and/or a relationship between the data and additional data.

Note that the location may be specified by a checksum associated with the data. Moreover, the expected content and/or the relationship may indicate the change relative to expected values for the data. Furthermore, the relationship may correspond to how the data is used by the API.

Additionally, the change may be detected based at least in part on one of: the API configuration, a security setting, and/or a transformation that converts raw data associated with the database into the data.

When the change is detected (operation 812), the computer may selectively perform the remedial action (operation 814), where the remedial action includes providing a notification with information specifying a data element associated with an API that is affected by the change.

In some embodiments, the remedial action may include updating an API configuration. Moreover, the computer may automatically and dynamically generate an updated API based at least in part on the updated API configuration.

In some embodiments of methods 200, 400, 600 and/or 800, there may be additional or fewer operations. Furthermore, the order of the operations may be changed, there may be different operations and/or two or more operations may be combined into a single operation.

Figure 9:
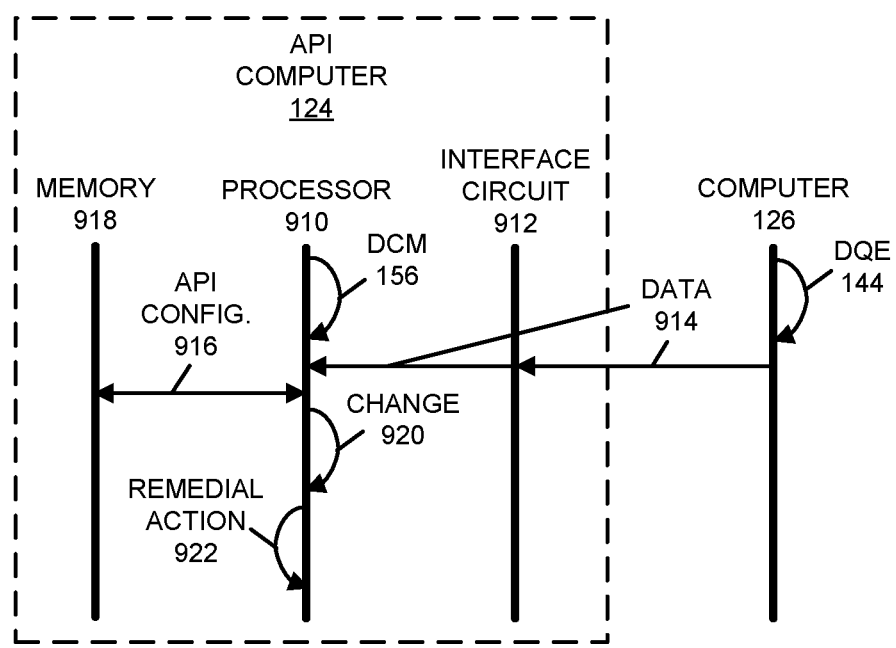
FIG. 9 is a drawing illustrating an example of communication among electronic devices in FIG. 1 in accordance with an embodiment of the present disclosure.

FIG. 9 presents a drawing illustrating an example of communication between API computer 124 and computer 126. Notably, a processor 910 in API computer 124 may execute DCM 156. Moreover, an interface circuit 912 in API computer 124 may receive data 914 from computer 126 (such as from DQE 144 executed on computer 126, as described previously with reference to FIGS. 6-7), which may provide data 914 to processor 910.

Based at least in part on program instructions associated with DCM 156, data 914 and/or API configuration 916 (which may be accessed in memory 918 in API computer 124), processor 710 may detect a change 920 in data 914 (such as a difference in data 914 relative to an expected content, e.g., value or range of values).

In response to detecting change 920, processor 920 may perform a remedial action 922. For example, processor 910 may instruct interface circuit 912 to provide a notification and/or a recommendation. Notably, the notification may include information specifying a data element associated with an API that is affected by change 920. Moreover, the recommendation may include a suggested update to API configuration 916, which may be used to automatically and dynamically generate an updated API (as described previously with reference to FIGS. 4-5).

While FIGS. 3, 5, 7 and 9 illustrate communication between components using unidirectional or bidirectional communication with lines having single arrows or double arrows, in general the communication in a given operation in these figures may involve unidirectional or bidirectional communication.

We now describe embodiments of an electronic device, which may perform at least some of the operations in the schema techniques, the generating techniques, the query techniques and/or the monitoring techniques. FIG. 10 presents a block diagram illustrating an example of an electronic device 1000 in accordance with some embodiments, such as electronic device 110, electronic device 112, access point 114, base station 116, application computer 122, API computer 124, computer 126, computer system 128, etc. This electronic device includes processing subsystem 1010, memory subsystem 1012, and networking subsystem 1014. Processing subsystem 1010 includes one or more devices configured to perform computational operations. For example, processing subsystem 1010 can include one or more microprocessors, ASICs, microcontrollers, programmable-logic devices, one or more graphics process units (GPUs) and/or one or more digital signal processors (DSPs).

Memory subsystem 1012 includes one or more devices for storing data and/or instructions for processing subsystem 1010 and networking subsystem 1014. For example, memory subsystem 1012 can include dynamic random access memory (DRAM), static random access memory (SRAM), and/or other types of memory. In some embodiments, instructions for processing subsystem 1010 in memory subsystem 1012 include: one or more program modules or sets of instructions (such as program instructions 1022 or operating system 1024), which may be executed by processing subsystem 1010. Note that the one or more computer programs may constitute a computer-program mechanism. Moreover, instructions in the various modules in memory subsystem 1012 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1010.

In addition, memory subsystem 1012 can include mechanisms for controlling access to the memory. In some embodiments, memory subsystem 1012 includes a memory hierarchy that comprises one or more caches coupled to a memory in electronic device 1000. In some of these embodiments, one or more of the caches is located in processing subsystem 1010.

In some embodiments, memory subsystem 1012 is coupled to one or more high-capacity mass-storage devices (not shown). For example, memory subsystem 1012 can be coupled to a magnetic or optical drive, a solid-state drive, or another type of mass-storage device. In these embodiments, memory subsystem 1012 can be used by electronic device 1000 as fast-access storage for often-used data, while the mass-storage device is used to store less frequently used data.

Networking subsystem 1014 includes one or more devices configured to couple to and communicate on a wired and/or wireless network (i.e., to perform network operations), including: control logic 1016, an interface circuit 1018 and one or more antennas 1020 (or antenna elements) and/or input/output (I/O) port 1030. (While FIG. 10 includes one or more antennas 1020, in some embodiments electronic device 1000 includes one or more nodes, such as nodes 1008, e.g., a network node that can be coupled or connected to a network or link, or an antenna node or a pad that can be coupled to the one or more antennas 1020. Thus, electronic device 1000 may or may not include the one or more antennas 1020.) For example, networking subsystem 1014 can include a Bluetooth™ networking system, a cellular networking system (e.g., a 3G/4G/5G network such as UMTS, LTE, etc.), a universal serial bus (USB) networking system, a networking system based on the standards described in IEEE 802.11 (e.g., a Wi-Fi® networking system), an Ethernet networking system, a cable modem networking system, and/or another networking system.

Networking subsystem 1014 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between the electronic devices does not yet exist. Therefore, electronic device 1000 may use the mechanisms in networking subsystem 1014 for performing simple wireless communication between the electronic devices, e.g., transmitting advertising or beacon frames and/or scanning for advertising frames transmitted by other electronic devices as described previously.

Within electronic device 1000, processing subsystem 1010, memory subsystem 1012, and networking subsystem 1014 are coupled together using bus 1028. Bus 1028 may include an electrical, optical, and/or electro-optical connection that the subsystems can use to communicate commands and data among one another. Although only one bus 1028 is shown for clarity, different embodiments can include a different number or configuration of electrical, optical, and/or electro-optical connections among the subsystems.

In some embodiments, electronic device 1000 includes a display subsystem 1026 for displaying information on a display, which may include a display driver and the display, such as a liquid-crystal display, a multi-touch touchscreen, etc.

Electronic device 1000 can be (or can be included in) any electronic device with at least one network interface. For example, electronic device 1000 can be (or can be included in): a computer system (such as a cloud-based computer system or a distributed computer system), a desktop computer, a laptop computer, a subnotebook/netbook, a server, a tablet computer, a smartphone, a cellular telephone, a smartwatch, a consumer-electronic device, a portable computing device, an access point, a transceiver, a router, a switch, communication equipment, a computer network device, a stack of computer network devices, a controller, test equipment, a printer, and/or another electronic device.

Although specific components are used to describe electronic device 1000, in alternative embodiments, different components and/or subsystems may be present in electronic device 1000. For example, electronic device 1000 may include one or more additional processing subsystems, memory subsystems, networking subsystems, and/or display subsystems. Additionally, one or more of the subsystems may not be present in electronic device 1000. Moreover, in some embodiments, electronic device 1000 may include one or more additional subsystems that are not shown in FIG. 10, such as a user-interface subsystem 1032. Also, although separate subsystems are shown in FIG. 10, in some embodiments some or all of a given subsystem or component can be integrated into one or more of the other subsystems or component(s) in electronic device 1000. For example, in some embodiments program instructions 1022 are included in operating system 1024 and/or control logic 1016 is included in interface circuit 1018.

Moreover, the circuits and components in electronic device 1000 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit (which is sometimes referred to as a 'communication circuit') may implement some or all of the functionality of networking subsystem 1014 or, more generally, of electronic device 1000. The integrated circuit may include hardware and/or software mechanisms that are used for transmitting wireless signals from electronic device 1000 and receiving signals at electronic device 1000 from other electronic devices. Aside from the mechanisms herein described, radios are generally known in the art and hence are not described in detail. In general, networking subsystem 1014 and/or the integrated circuit can include any number of radios. Note that the radios in multiple-radio embodiments function in a similar way to the described single-radio embodiments.

In some embodiments, networking subsystem 1014 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals)

In some embodiments, an output of a process for designing the integrated circuit, or a portion of the integrated circuit, which includes one or more of the circuits described herein may be a computer-readable medium such as, for example, a magnetic tape or an optical or magnetic disk. The computer-readable medium may be encoded with data structures or other information describing circuitry that may be physically instantiated as the integrated circuit or the portion of the integrated circuit. Although various formats may be used for such encoding, these data structures are commonly written in: Caltech Intermediate Format (CIF), Calma GDS II Stream Format (GDSII) or Electronic Design Interchange Format (EDIF). Those of skill in the art of integrated circuit design can develop such data structures from schematics of the type detailed above and the corresponding descriptions and encode the data structures on the computer-readable medium. Those of skill in the art of integrated circuit fabrication can use such encoded data to fabricate integrated circuits that include one or more of the circuits described herein.

While the preceding discussion used Ethernet, a cellular-telephone communication protocol and a Wi-Fi communication protocol as an illustrative example, in other embodiments a wide variety of communication protocols and, more generally, wired and/or wireless communication techniques may be used. Thus, the disclosed techniques may be used with a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the disclosed techniques may be implemented using program instructions 1022, operating system 1024 (such as a driver for interface circuit 1018) or in firmware in interface circuit 1018. Alternatively or additionally, at least some of the operations in the disclosed techniques may be implemented in a physical layer, such as hardware in interface circuit 1018.

In the preceding description, we refer to 'some embodiments.' Note that' some embodiments' describes a subset of all of the possible embodiments, but does not always specify the same subset of embodiments. Moreover, note that numerical values in the preceding embodiments are illustrative examples of some embodiments. In other embodiments of the disclosed techniques, different numerical values may be used.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer system, comprising:
a network interface configured to communicate with a second computer system that implements a data-query engine for a database;
a processor; and
memory configured to store program instructions, wherein, when executed by the processor, the program instructions cause the computer system to perform operations comprising:
receiving, at the network interface, data associated with the second computer system and the database;
detecting a change in the data based at least in part on one or more of: a schedule of when to check for the change; a location in the database associated with the data; expected content of the data; or a relationship between the data and additional data, wherein the detecting comprises providing, via the second computer system, one or more calls to the database, wherein the computer system does not have knowledge of a schema of the database, wherein the detecting is based at least in part on a structure of an application programming interface (API) that is affected by the change, wherein the data in the database for the API is accessed via a single endpoint that is common to multiple different APIs having different API configurations, the APIs comprise the API, and the data is accessed based at least in part on an API configuration of the API, and wherein accessing the single endpoint comprises providing a call to the single endpoint with an identifier of the API configuration to execute, and in response the single endpoint interprets the API configuration and provides an associated call to the database; and
when the change is detected, performing a remedial action, wherein the remedial action comprises providing a notification with information specifying a data element associated with the API that is affected by the change.

2. The computer system of claim 1, wherein the location is specified by a checksum associated with the data.

3. The computer system of claim 1, wherein the expected content, the relationship or both indicate the change relative to expected values for the data.

4. The computer system of claim 1, wherein the relationship corresponds to how the data is used by the API.

5. The computer system of claim 1, wherein the change is detected based at least in part on one of: the API configuration, a security setting, or a transformation that converts raw data associated with the database into the data.

6. The computer system of claim 1, wherein the remedial action comprises updating an API configuration.

7. The computer system of claim 6, wherein the operations comprise automatically and dynamically generating an updated API based at least in part on the updated API configuration.

8. The computer system of claim 1, wherein the second computer system is different from the computer system.

9. The computer system of claim 1, wherein the database is associated with electronic health record (EHR) software, and the database and the data comprise patient medical data.

10. A non-transitory computer-readable storage medium for use in conjunction with a computer system, the computer-readable storage medium storing program instructions that, when executed by the computer system, cause the computer system to perform operations comprising:
receiving data associated with a second computer system that implements a data query engine for a database and that is associated with the database;
detecting a change in the data based at least in part on one or more of: a schedule of when to check for the change; a location in the database associated with the data; expected content of the data; or a relationship between the data and additional data, wherein the detecting comprises providing, via the second computer system, one or more calls to the database, wherein the computer system does not have knowledge of a schema of the database, wherein the detecting is based at least in part on a structure of an application programming interface (API) that is affected by the change, wherein the data in the database for the API is accessed via a single endpoint that is common to multiple different APIs having different API configurations, the APIs comprise the API, and the data is accessed based at least in part on an API configuration of the API, and wherein accessing the single endpoint comprises providing a call to the single endpoint with an identifier of the API configuration to execute, and in response the single endpoint interprets the API configuration and provides an associated call to the database; and when the change is detected, performing a remedial action, wherein the remedial action comprises providing a notification with information specifying a data element associated with the API that is affected by the change.

11. The non-transitory computer-readable storage medium of claim 10, wherein the location is specified by a checksum associated with the data.

12. The non-transitory computer-readable storage medium of claim 10, wherein the expected content, the relationship or both indicate the change relative to expected values for the data.

13. The non-transitory computer-readable storage medium of claim 10, wherein the relationship corresponds to how the data is used by the API.

14. The non-transitory computer-readable storage medium of claim 10, wherein the change is detected based at least in part on one of: the API configuration, a security setting, or a transformation that converts raw data associated with the database into the data.

15. The non-transitory computer-readable storage medium of claim 10, wherein the remedial action comprises updating an API configuration.

16. The non-transitory computer-readable storage medium of claim 15, wherein the operations comprise automatically and dynamically generating an updated API based at least in part on the updated API configuration.

17. The non-transitory computer-readable storage medium of claim 10, wherein the database is associated with electronic health record (EHR) software, and the database and the data comprise patient medical data.

18. A method for detecting a change and selectively performing a remedial action, comprising: by a computer system:

receiving data associated with a second computer system that implements a data query engine for a database and that is associated with the database;

detecting the change in the data based at least in part on one or more of: a schedule of when to check for the change; a location in the database associated with the data; expected content of the data; or a relationship between the data and additional data, wherein the detecting comprises providing, via the second computer system, one or more calls to the database, wherein the computer system does not have knowledge of a schema of the database, wherein the detecting is based at least in part on a structure of an application programming interface (API) that is affected by the change, wherein the data in the database for the API is accessed via a single endpoint that is common to multiple different APIs having different API configurations, the APIs comprise the API, and the data is accessed based at least in part on an API configuration of the API, and wherein accessing the single endpoint comprises providing a call to the single endpoint with an identifier of the API configuration to execute, and in response the single endpoint interprets the API configuration and provides an associated call to the database; and when the change is detected, performing a remedial action, wherein the remedial action comprises providing a notification with information specifying a data element associated with the API that is affected by the change.

19. The method of claim 18, wherein the location is specified by a checksum associated with the data.

20. The method of claim 18, wherein the change is detected based at least in part on one of: the API configuration, a security setting, or a transformation that converts raw data associated with the database into the data.

* * * * *